(12) United States Patent
Tanaka

(10) Patent No.: US 10,722,206 B2
(45) Date of Patent: Jul. 28, 2020

(54) X-RAY HIGH VOLTAGE DEVICE AND X-RAY IMAGE DIAGNOSIS APPARATUS

(71) Applicant: CANON MEDICAL SYSTEMS CORPORATION, Otawara-shi (JP)

(72) Inventor: Kimio Tanaka, Nasushiobara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 64 days.

(21) Appl. No.: 16/107,134

(22) Filed: Aug. 21, 2018

(65) Prior Publication Data

US 2019/0059844 A1 Feb. 28, 2019

(30) Foreign Application Priority Data

Aug. 22, 2017 (JP) .................. 2017-159765

(51) Int. Cl.
| | |
|---|---|
| *A61B 6/00* | (2006.01) |
| *H02M 7/5387* | (2007.01) |
| *H02M 1/08* | (2006.01) |
| *H02M 3/337* | (2006.01) |
| *H02M 1/00* | (2006.01) |

(Continued)

(52) U.S. Cl.
CPC .............. *A61B 6/56* (2013.01); *H02M 1/083* (2013.01); *H02M 3/337* (2013.01); *H02M 7/53871* (2013.01); *A61B 6/032* (2013.01); *A61B 6/06* (2013.01); *A61B 6/4035* (2013.01); *H02M 2001/0054* (2013.01); *H02M 2001/0058* (2013.01)

(58) Field of Classification Search
CPC ........... A61B 6/56; A61B 6/06; A61B 6/4035; A61B 6/032; H02M 3/337; H02M 7/53871; H02M 1/083; H02M 2001/0058; H02M 2001/0054
USPC ........................................... 378/101
See application file for complete search history.

(56) References Cited

U.S. PATENT DOCUMENTS

| | | | | |
|---|---|---|---|---|
| 5,717,584 | A * | 2/1998 | Rajashekara | ....... H02M 7/5387 363/132 |
| 6,388,397 | B1 * | 5/2002 | Iwahori | ................ H05B 41/282 315/224 |
| 7,586,294 | B2 | 9/2009 | Endo | |

(Continued)

FOREIGN PATENT DOCUMENTS

| | | |
|---|---|---|
| JP | 10-80151 | 3/1998 |
| JP | 2004-72893 | 3/2004 |

(Continued)

*Primary Examiner* — David P Porta
*Assistant Examiner* — Gisselle M Gutierrez
(74) *Attorney, Agent, or Firm* — Oblon, McClelland, Maier & Neustadt, L.L.P.

(57) ABSTRACT

An X-ray high voltage device according to an embodiment includes: an inverter circuit including a plurality of switching elements; acquiring circuitry configured to acquire information about an inverter current flowing through the inverter circuit; and controlling circuitry configured to determine, on the basis of the information about the inverter current, a first point in time at which the inverter current becomes substantially 0 and to exercise control by implementing zero current switching control on the switching elements at the first point in time and implementing zero voltage switching control on the switching elements at a second point in time excluding the first point in time.

8 Claims, 12 Drawing Sheets

(51) Int. Cl.
 *A61B 6/03* (2006.01)
 *A61B 6/06* (2006.01)

(56) References Cited

U.S. PATENT DOCUMENTS

| | | | | |
|---|---|---|---|---|
| 2013/0043854 | A1* | 2/2013 | Tran | H02M 3/155 |
| | | | | 323/284 |
| 2014/0319919 | A1* | 10/2014 | Fu | H02M 7/539 |
| | | | | 307/82 |
| 2015/0023063 | A1* | 1/2015 | Perreault | H02M 3/337 |
| | | | | 363/17 |
| 2015/0229200 | A1* | 8/2015 | Schwartz | H02M 3/3376 |
| | | | | 363/21.03 |
| 2015/0244284 | A1* | 8/2015 | Fu | H02M 7/537 |
| | | | | 363/41 |
| 2016/0065073 | A1* | 3/2016 | Katsuki | H02M 3/158 |
| | | | | 323/271 |
| 2017/0317601 | A1* | 11/2017 | Jin | H02M 3/28 |
| 2018/0069490 | A1* | 3/2018 | Fu | H02M 7/539 |

FOREIGN PATENT DOCUMENTS

| | | |
|---|---|---|
| JP | 2007-28827 | 2/2007 |
| JP | 2009-17749 | 1/2009 |
| JP | 5667766 | 2/2015 |

* cited by examiner

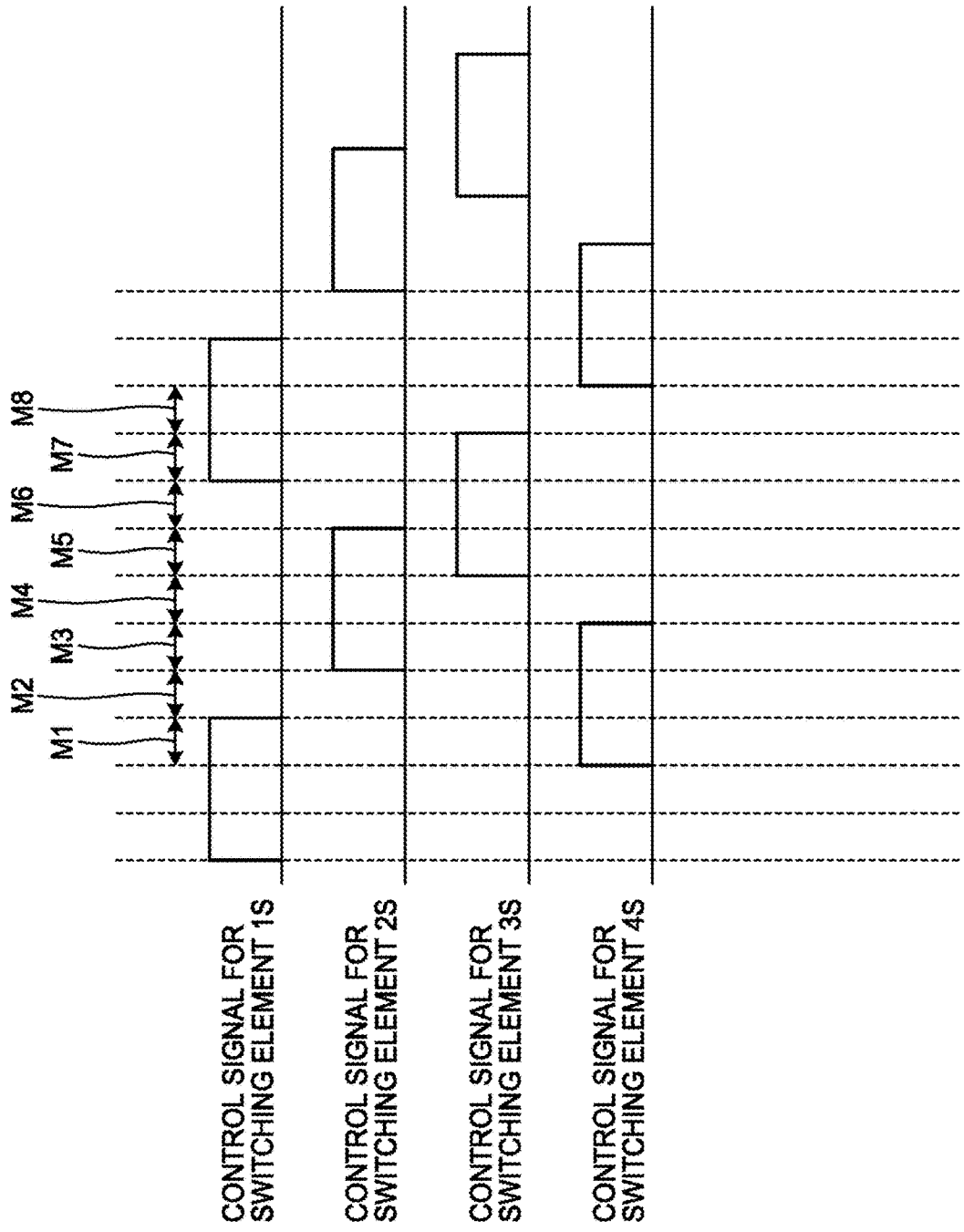

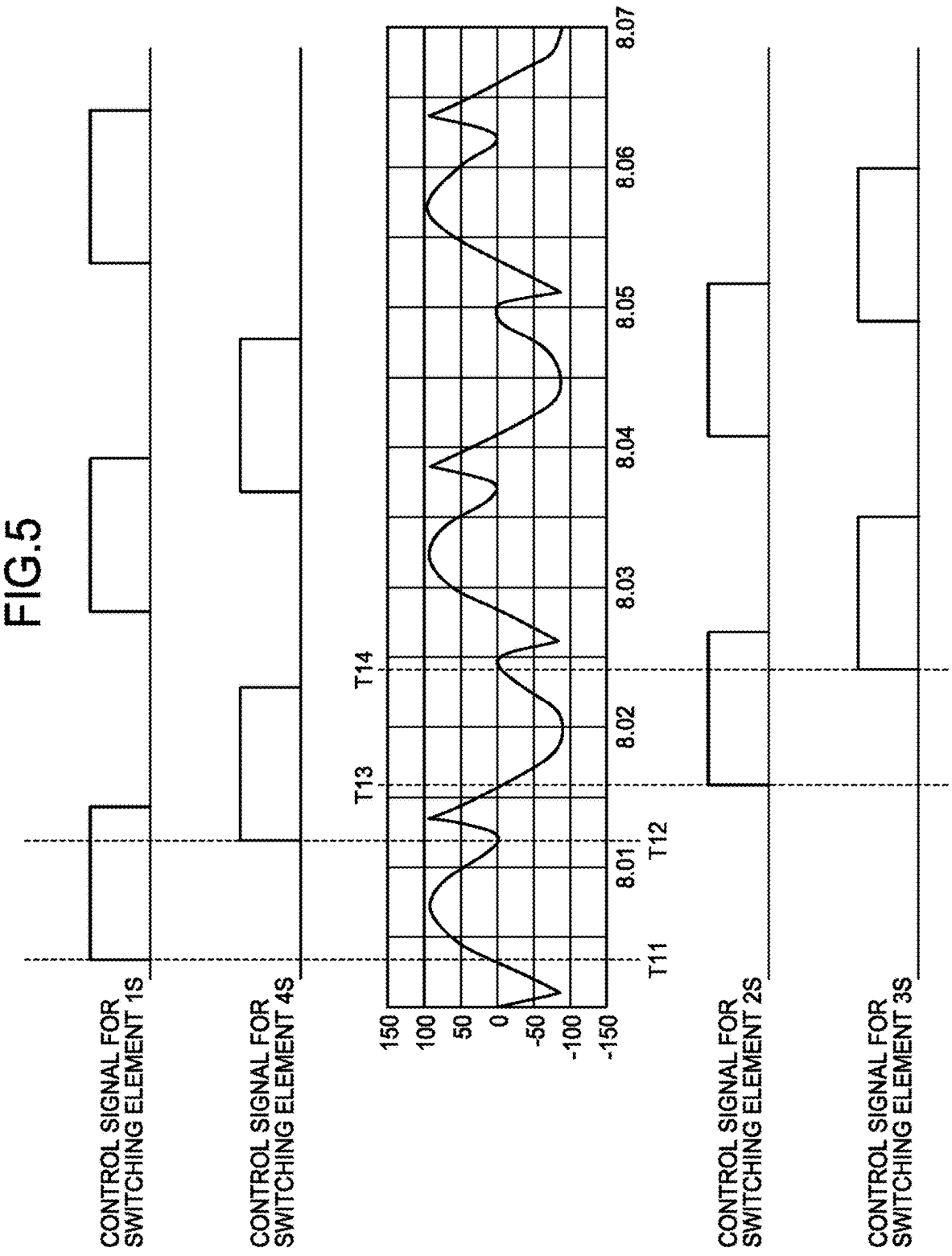

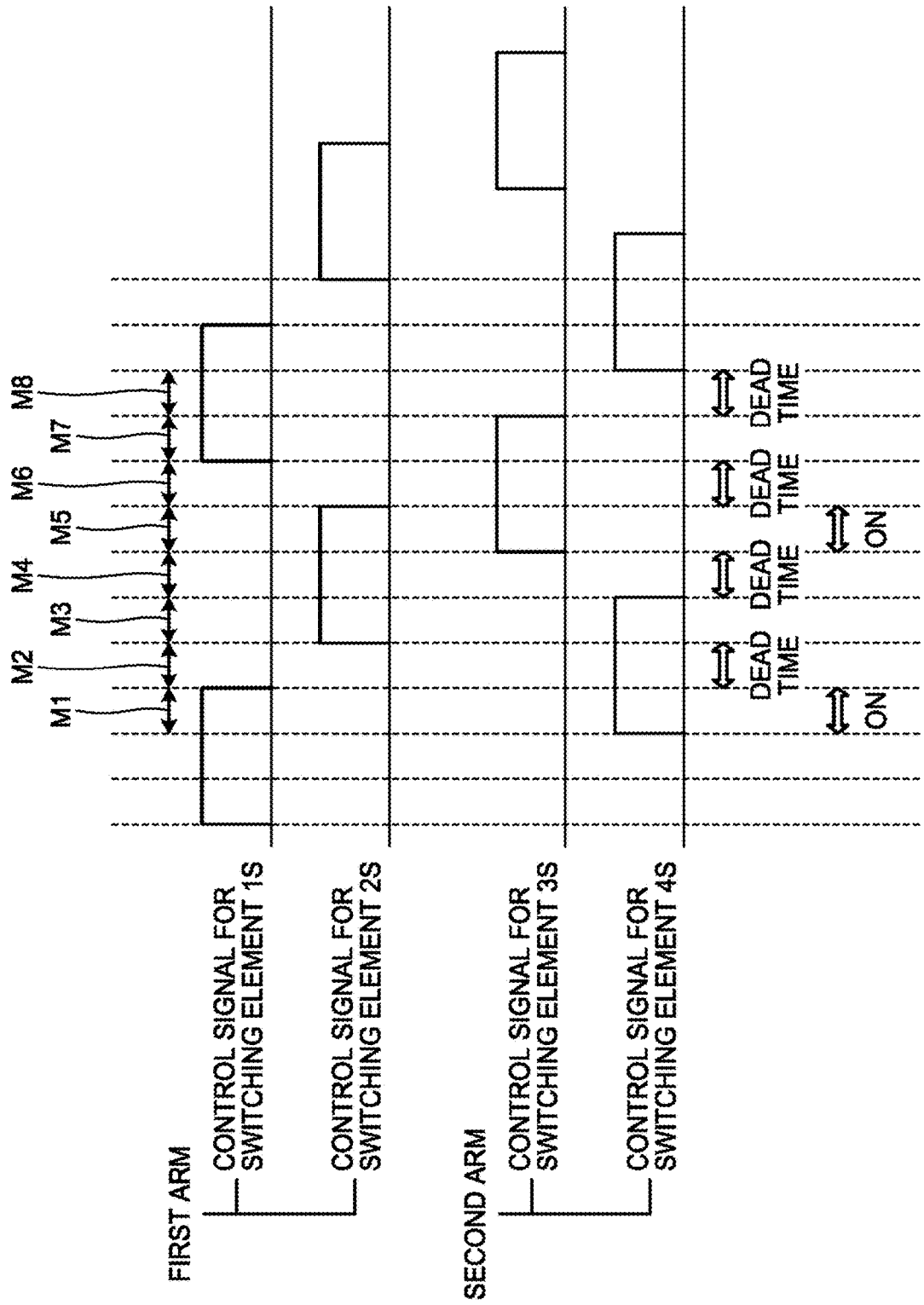

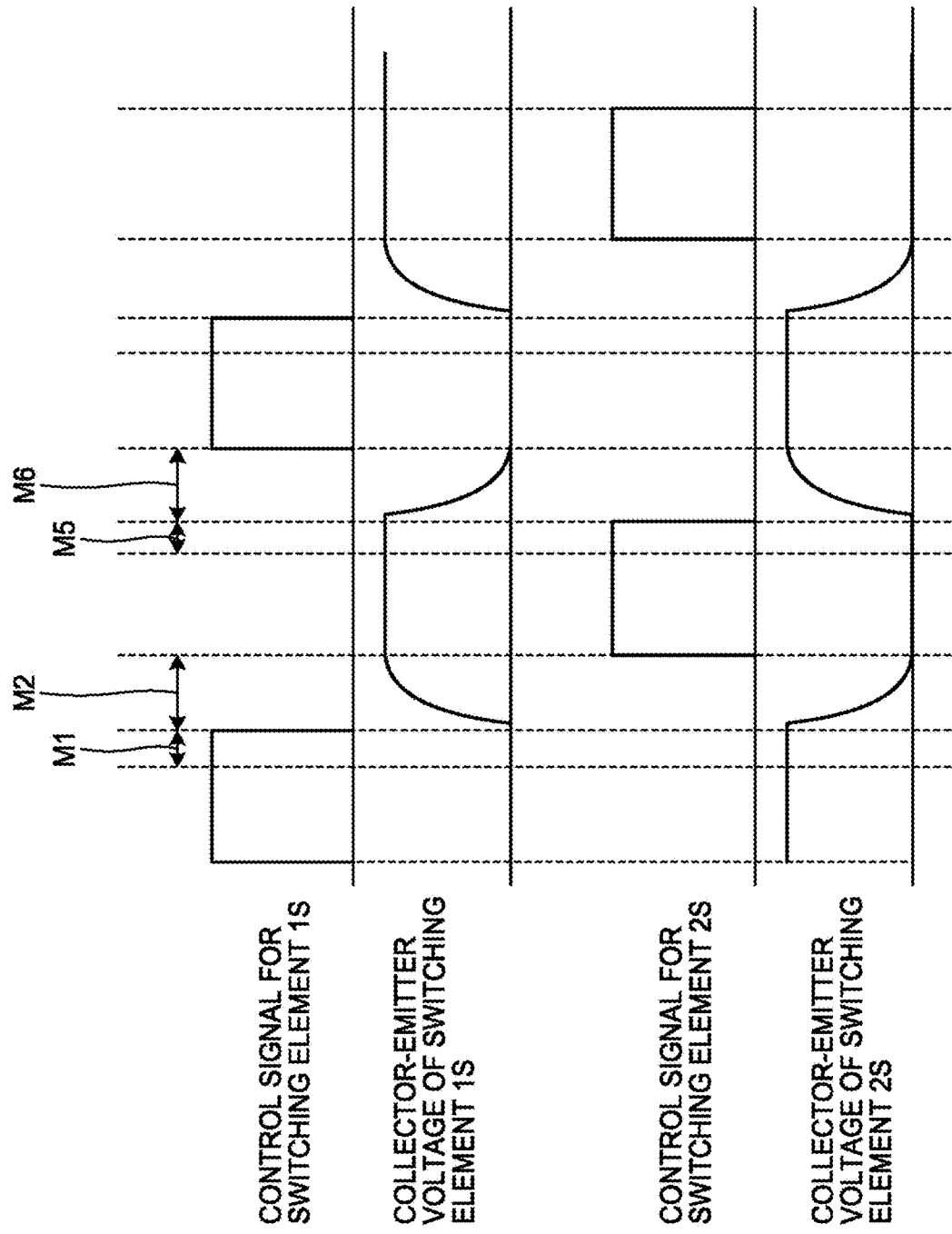

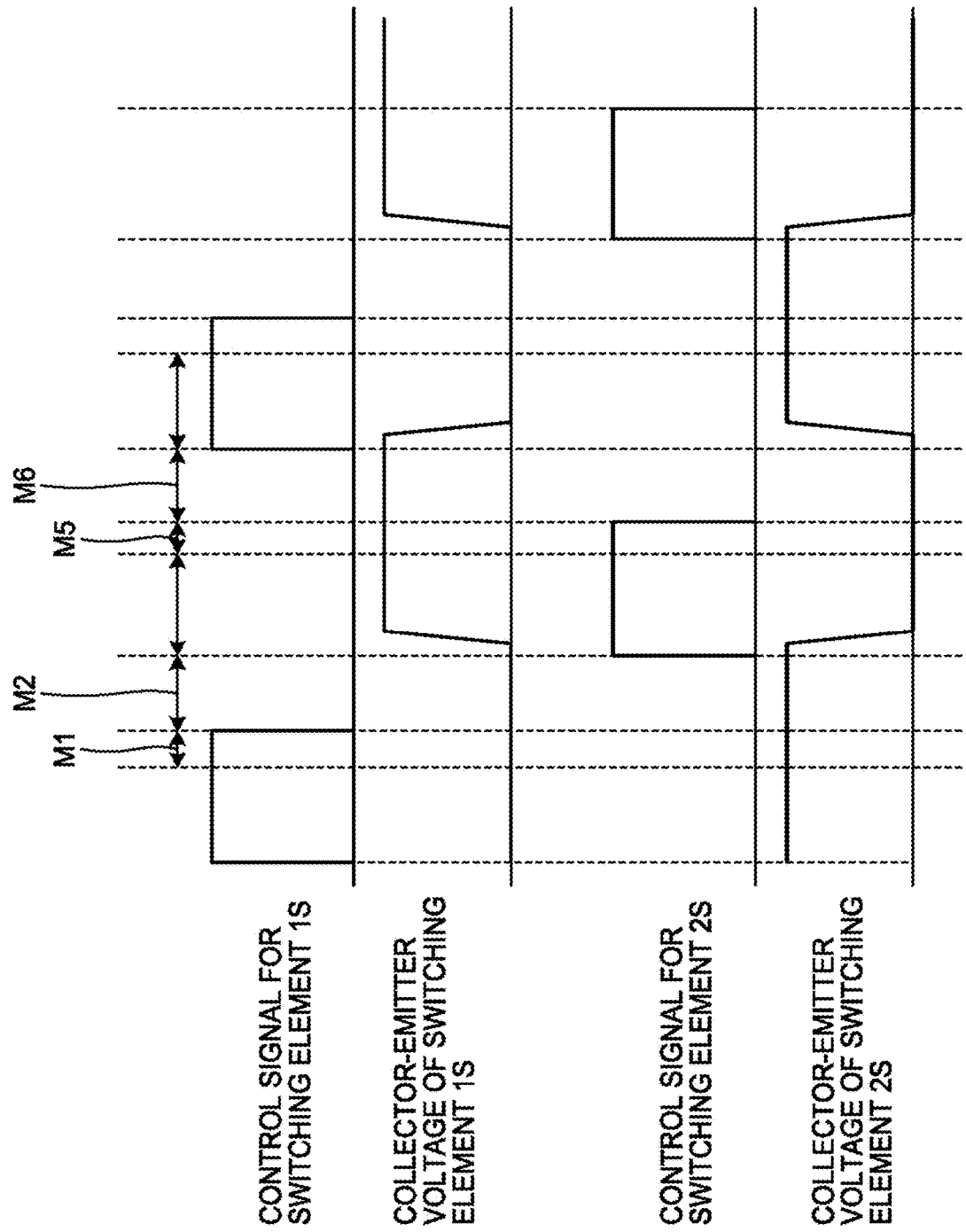

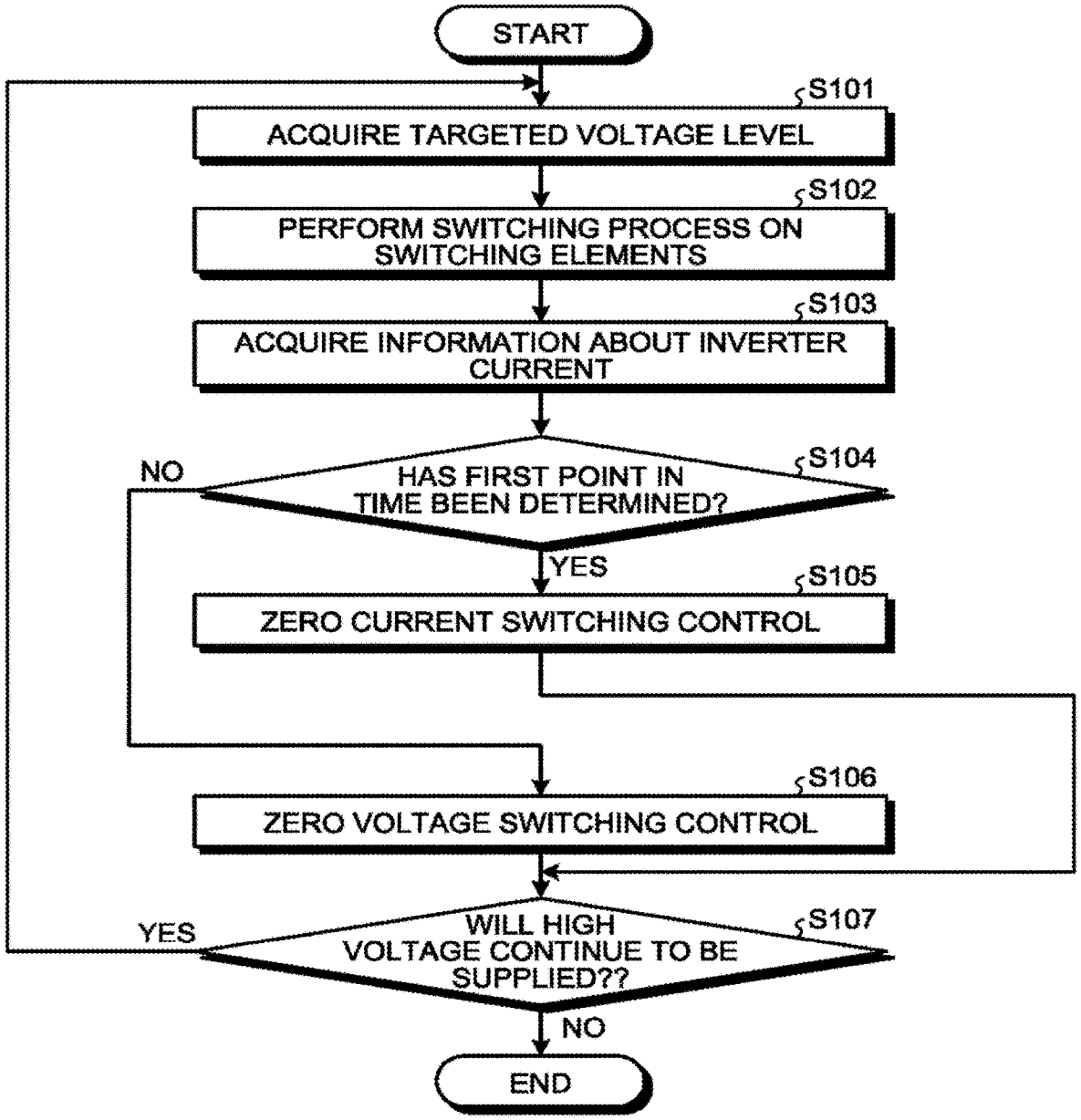

X-RAY HIGH VOLTAGE DEVICE AND X-RAY IMAGE DIAGNOSIS APPARATUS

CROSS-REFERENCE TO RELATED APPLICATIONS

This application is based upon and claims the benefit of priority from Japanese Patent Application No. 2017-159765, filed on Aug. 22, 2017; the entire contents of which are incorporated herein by reference.

FIELD

Embodiments described herein related generally to an X-ray high voltage device and an X-ray image diagnosis apparatus.

BACKGROUND

X-ray high voltage devices are configured to control the voltage supplied to an X-ray tube. For example, an X-ray high voltage device is configured to control output voltage by switching on and off switching elements included in an inverter circuit. When the switching process is performed at a higher frequency, advantages are achieved where output voltage ripples are reduced and where the structure (coils, a transformer, capacitors, and the like) of the X-ray high voltage device can be kept compact. However, because the number of times the switching elements are switched on and off increases, losses that occur during the switching process (hereinafter, "switching losses") increase. In this regard, for the purpose of reducing such switching losses, it is possible to make use of soft switching control such as Zero Voltage Switching (ZVS) control and Zero Current Switching (ZCS) control.

The zero voltage switching control is a controlling method implemented to reduce switching losses, by which the voltage is caused to resonate as a result of storing and extracting an electric charge into and from a capacitor (a resonant capacitor) provided in parallel to a switching element, so that the switching process is performed at the time when the voltage of the switching element becomes substantially 0. In this situation, what extracts the electric charge from the resonant capacitor is an inverter current flowing through an inverter circuit. Thus, when the inverter current is small, it may be impossible, in some situations, to extract the electric charge from the resonant capacitor until the voltage becomes substantially 0. For example, when the output power of the X-ray high voltage device is small or the like, it may be impossible to implement the zero voltage switching control while the load is small, in some situations. In other words, even when an attempt is made to implement the zero voltage switching control while the load is small, it is impossible to extract the electric charge from the resonant capacitor until the voltage becomes substantially 0. As a result, because the switching element is turned on while the voltage is not substantially 0, a switching loss occurs. Further, when the switching element is turned on while the voltage is not substantially 0, a short-circuit current may flow into the switching element due to the electric charge stored in the resonant capacitor and may damage the switching elements in some situations.

In contrast, the zero current switching control is a controlling method implemented to reduce switching losses, by which a switching process is performed at a time when the inverter current becomes substantially 0. In this situation, the X-ray high voltage device includes a high voltage transformer, mold resin, and the like, which substantially function as a capacitor. The electrostatic capacitance (a stray capacitance) of such a capacitor may cause the inverter current to have a current resonance. Thus, when the switching element is turned on while the electric current (hereinafter, "current") is not substantially 0, a switching loss occurs. Further, when the output power of the X-ray high voltage device is large or the like, it may be impossible, in some situations, to implement the zero current switching control while the load is large, due to the absence of the time at which the current becomes substantially 0.

BRIEF DESCRIPTION OF THE DRAWINGS

FIG. 3 is a chart for explaining phase shift control according to the first embodiment;

FIG. 5 is a drawing for explaining zero current switching control according to the first embodiment;

FIG. 8 is a chart for explaining zero voltage switching control according to the first embodiment;

FIG. 9 is a chart illustrating examples of control signals and voltage levels of switching elements according to the first embodiment;

FIG. 10 is another chart illustrating examples of control signals and voltage levels of switching elements according to the first embodiment;

FIG. 11 is a flowchart for explaining a flow in a series of processes performed by the X-ray CT apparatus according to the first embodiment.

DETAILED DESCRIPTION

An X-ray high voltage device comprises an inverter circuit, acquiring circuitry and controlling circuitry. The inverter circuit includes a plurality of switching elements. The acquiring circuitry is configured to acquire information about an inverter current flowing through the inverter circuit. The controlling circuitry is configured to determine, on a basis of the information about the inverter current, a first point in time at which the inverter current becomes substantially 0 and to exercise control by implementing zero current switching control on the switching elements at the first point in time and implementing zero voltage switching control on the switching elements at a second point in time excluding the first point in time.

Exemplary embodiments of the X-ray high voltage device and an X-ray image diagnosis apparatus will be explained in detail below, with reference to the accompanying drawings. The X-ray image diagnosis apparatus is an apparatus configured to generate a medical image by using X-rays. For example, the X-ray image diagnosis apparatus may be an X-ray diagnosis apparatus, an X-ray Computed Tomography (CT) apparatus, or the like. In the following sections, as an example, an X-ray CT apparatus including the X-ray high voltage device will be explained.

Figure 1:
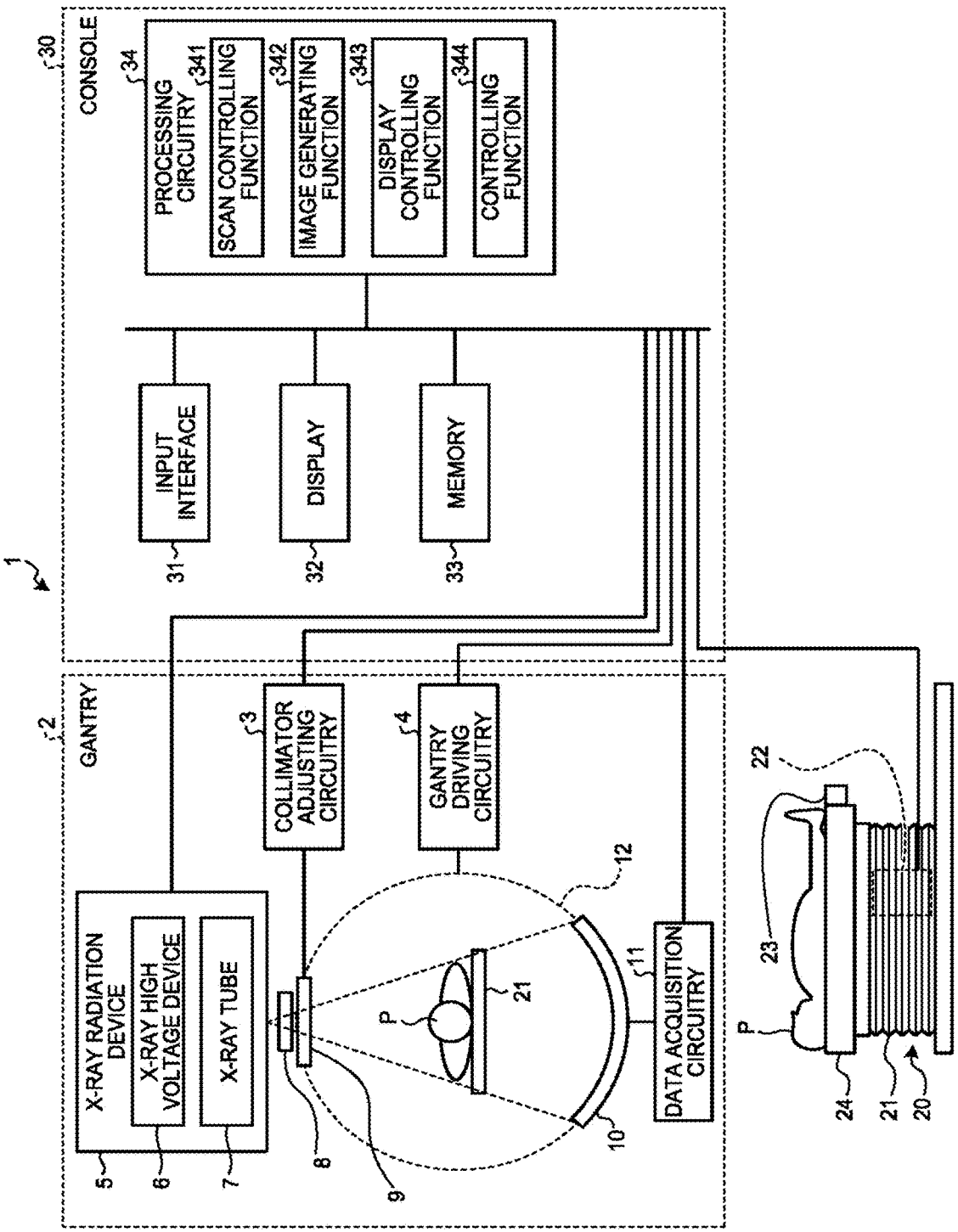
FIG. 1 is a block diagram illustrating an exemplary configuration of an X-ray Computed Tomography (CT) apparatus according to a first embodiment.

A configuration of an X-ray Computed Tomography (CT) apparatus 1 according to a first embodiment will be explained with reference to FIG. 1. FIG. 1 is a block diagram illustrating an exemplary configuration of the X-ray CT apparatus 1 according to the first embodiment. As illustrated in FIG. 1, the X-ray CT apparatus 1 includes a gantry 2, a couch 20, and a console 30. Possible configurations of the X-ray CT apparatus 1 are not limited to the configuration described below.

The gantry 2 includes collimator adjusting circuitry 3, gantry driving circuitry 4, an X-ray radiation device 5, a wedge 8, a collimator 9, an X-ray detector 10, data acquisition circuitry 11, and a rotating frame 12.

The collimator adjusting circuitry 3 is configured to adjust the radiation range of X-rays generated by the X-ray radiation device 5, by adjusting the opening degree and the position of the collimator 9. The collimator adjusting circuitry 3 is connected to the collimator 9 and includes a mechanism configured to adjust the opening degree and the position and a circuit configured to control the mechanism. For example, the mechanism includes a motor and a mechanical element configured to transmit the power generated by the motor to the collimator 9. Further, the abovementioned circuit includes, for example, a circuit configured to supply electric power and a control signal to the motor and a processor configured to control the circuit.

The gantry driving circuitry 4 is configured to cause the X-ray radiation device 5 and the X-ray detector 10 to revolve, by causing the rotating frame 12 to rotate and configured to tilt the gantry 2. The gantry driving circuitry 4 includes a mechanism configured to cause the rotating frame 12 to rotate, a mechanism configured to tilt the gantry 2, and a circuit configured to control these mechanisms. The mechanism includes, for example, a motor and a mechanical element configured to transmit the power generated by the motor to the rotating frame 12. Further, the abovementioned circuit includes, for example, a circuit configured to supply electric power and a control signal to the motor and a processor configured to control the circuit.

As illustrated in FIG. 1, the X-ray radiation device 5 includes an X-ray high voltage device 6 and an X-ray tube 7. The X-ray high voltage device 6 is a device configured to generate high voltage. A circuit configuration of the X-ray high voltage device 6 will be explained later. The X-ray tube 7 is a vacuum tube configured to emit thermo electrons from a negative pole (a filament) to a positive pole (a target), by using the high voltage supplied by the X-ray high voltage device 6.

The wedge 8 is a filter used for adjusting the dose of the X-rays radiated from the X-ray tube 7. More specifically, the wedge 8 is a filter configured to pass and attenuate the X-rays radiated from the X-ray tube 7, so that the X-rays radiated from the X-ray tube 7 onto an examined subject (hereinafter, "patient") P have a predetermined distribution. For example, the wedge 8 may be a wedge filter or a bow-tie filter and is obtained by processing aluminum or the like so as to have a predetermined target angle and a predetermined thickness.

The collimator 9 is configured with lead plates or the like used for narrowing down the radiation range of the X-rays that have passed through the wedge 8. Slits are formed by combining the plurality of lead plates or the like. The opening degree and the position of the collimator 9 are adjusted by the collimator adjusting circuitry 3.

The X-ray detector 10 is configured to detect the X-rays that were radiated from the X-ray radiation device 5 and have passed through the patient P and to output a signal corresponding to the detected X-ray dose to the data acquisition circuitry 11. For example, the X-ray detector 10 includes a plurality of rows of X-ray detecting elements in each of which a plurality of X-ray detecting elements are arranged in a channel direction along an arc centered on a focal point of the X-ray tube 7. For example, the X-ray detector 10 has a structure in which the plurality of rows of X-ray detecting elements are arranged in a slice direction (a row direction), the rows each being made up of the plurality of X-ray detecting elements arranged in the channel direction. Further, for example, the X-ray detector 10 may be an indirect-conversion-type detector including a grid, a scintillator array, and an optical sensor array. The scintillator array includes a plurality of scintillators. Each of the scintillators includes a scintillator crystal that outputs light having photons in a quantity corresponding to the dose of the X-rays that have become incident thereto. The grid is arranged on such a surface of the scintillator array positioned the X-ray incident side and includes an X-ray blocking plate configured to absorb scattered X-rays. The optical sensor array has a converting function to output an electrical signal corresponding to the quantity of the light from the scintillators and includes, for example, an optical sensor such as a PhotoMultiplier Tube (PMT). Alternatively, the X-ray detector 10 may be a direct-conversion-type detector including a semiconductor element configured to convert X-rays that have become incident thereto into an electric signal.

The data acquisition circuitry 11 is a Data Acquisition System (DAS). The data acquisition circuitry 11 includes: an amplifier configured to perform an amplifying process on electrical signals output from the X-ray detecting elements included in the X-ray detector 10; and an Analog/Digital (A/D) converter configured to convert the electrical signals into digital signals. The data acquisition circuitry 11 is configured to generate detection data. For example, the data acquisition circuitry 11 is realized by using a processor.

The rotating frame 12 is an annular frame configured to support the X-ray tube 7 and the X-ray detector 10 so as to oppose each other and configured to cause the gantry driving circuitry 4 to rotate the X-ray tube 7 and the X-ray detector 10. In addition to the X-ray tube 7 and the X-ray detector 10, the rotating frame 12 is further provided with, and is configured to support, the X-ray high voltage device 6 and the data acquisition circuitry 11. Further, the detection data generated by the data acquisition circuitry 11 is transmitted through optical communication from a transmitter including a light emitting diode (LED) and being provided for the rotating frame 12, to a receiver including a photo diode and being provided in a non-rotating part (e.g., a fixed frame) of the gantry 2, so as to be further transferred to the console 30. The method for transmitting the detection data from the rotating frame 12 to the non-rotating part of the gantry 2 is not limited to optical communication. It is acceptable to use any contactless data transmission method.

The couch 20 is a device on which the patient P to be scanned is placed and which is configured to move the patient P. The couch 20 includes a base 21, a couch driving device 22, a tabletop 23, and a supporting frame 24. The base 21 is a casing configured to support the supporting frame 24 in such a manner that the supporting frame 24 is movable in vertical directions. The couch driving device 22 is either a motor or an actuator configured to move the tabletop 23 on which the patient P is placed, in the long-axis directions of the tabletop 23. The tabletop 23 provided on the top face of the supporting frame 24 is a plate on which the patient P is placed. In addition to the tabletop 23, the couch driving device 22 may also be configured to move the supporting frame 24 in the long-axis directions of the tabletop 23.

The console 30 includes an input interface 31, a display 32, a memory 33, and processing circuitry 34.

The input interface 31 is configured to receive various types of input operations from an operator, to convert the received input operations into electrical signals, and to output the electrical signals to the processing circuitry 34. For example, the input interface 31 receives, from the operator, scan conditions such as an X-ray tube voltage level and an X-ray tube current level, as well as reconstruction conditions used for reconstructing a CT image, image processing conditions used for generating a post-processing image from the CT image, and the like. For example, the input interface 31 is realized with a mouse, a keyboard, a trackball, a switch, a button, a joystick, a touch panel, and/or the like.

The display 32 is configured to display various types of information. For example, the display 32 is configured to output a CT image generated by the processing circuitry 34, a Graphical User Interface (GUI) used for receiving various types of operations from the operator, and the like. For example, the display 32 may be a liquid crystal display device, a Cathode Ray Tube (CRT) display device, or the like.

The memory 33 is realized by using, for example, a semiconductor memory element such as a Random Access Memory (RAM), a flash memory, or the like, or a hard disk, an optical disk, or the like. For example, the memory 33 is configured to store therein projection data and reconstructed image data. Further, for example, the memory 33 stores therein computer programs (hereinafter, "programs") used by circuits to realize the functions thereof.

The processing circuitry 34 is configured to control operations of the entirety of the X-ray CT apparatus 1. For example, the processing circuitry 34 includes a scan controlling function 341, an image generating function 342, a display controlling function 343, and a controlling function 344. For example, the processing circuitry 34 may be realized by using a processor.

For example, by reading and executing a program corresponding to the scan controlling function 341 from the memory 33, the processing circuitry 34 is configured to perform a scan by controlling the X-ray CT apparatus 1. In this situation, for example, the scan controlling function 341 is capable of performing a conventional scan, a helical scan, or a scan that uses any of various types of methods such as a step-and-shoot method.

More specifically, the scan controlling function 341 moves the patient P to the inside of an image taking opening of the gantry 2, by controlling the couch driving device 22.

Further, by controlling the X-ray high voltage device 6, the scan controlling function 341 supplies the high voltage to the X-ray tube 7. For example, the scan controlling function 341 informs the X-ray high voltage device 6 of the X-ray tube voltage level indicated in the scan conditions, so that voltage at the targeted level is supplied to the X-ray tube 7. Further, the scan controlling function 341 is configured to adjust the opening degree and the position of the collimator 9, by controlling the collimator adjusting circuitry 3. In addition, the scan controlling function 341 is configured to cause the rotating frame 12 to rotate, by controlling the gantry driving circuitry 4. Also, the scan controlling function 341 is configured to cause the data acquisition circuitry 11 to acquire the projection data.

Further, for example, by reading and executing a program corresponding to the image generating function 342 from the memory 33, the processing circuitry 34 is configured to generate data acquired by performing, on the detection data output from the data acquisition circuitry 11, one or more pre-processing processes such as a logarithmic conversion process, an offset correcting process, an inter-channel sensitivity correcting process, a beam hardening correcting process, and/or the like. The data (the detection data) before the pre-processing processes and the data after the pre-processing processes may collectively be referred to as projection data. Further, for example, the image generating function 342 is configured to generate CT image data. More specifically, the image generating function 342 generates the CT image data by implementing a reconstructing process that uses a filter correction back projection method or successive approximation reconstruction method on the projection data resulting from the pre-processing processes. Further, the image generating function 342 is configured to convert the CT image data into tomographic image data on an arbitrary cross-sectional plane or three-dimensional image data, on the basis of an input operation received from the operator via the input interface 31.

Further, for example, by reading and executing a program corresponding to the display controlling function 343 from the memory 33, the processing circuitry 34 is configured to cause the display 32 to display the CT image. Further, for example, by reading and executing a program corresponding to the controlling function 344 from the memory 33, the processing circuitry 34 is configured to control the various types of functions of the processing circuitry 34, on the basis of an input operation received from the operator via the input interface 31.

Figure 2:
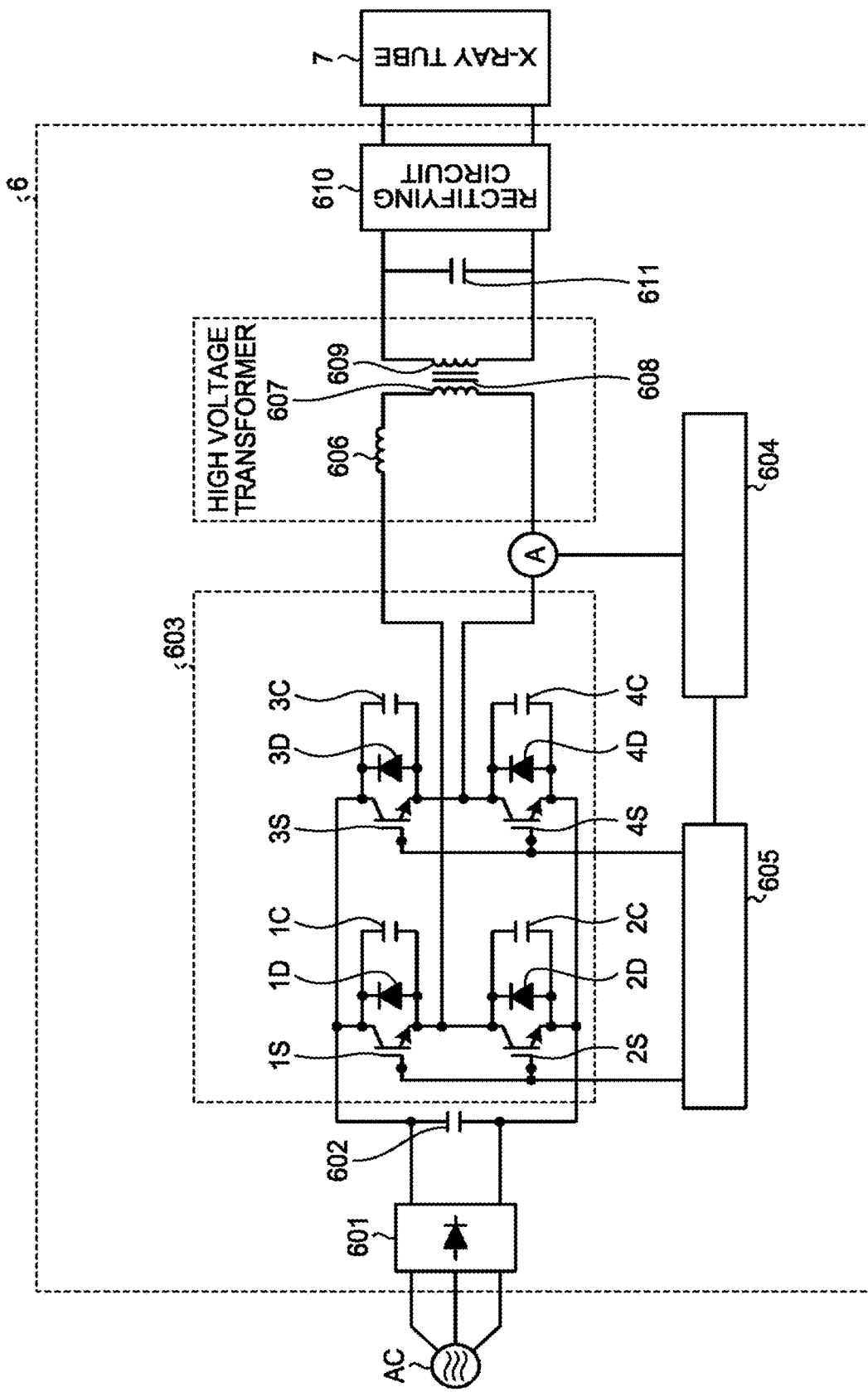
FIG. 2 is a diagram illustrating an example of a circuit configuration of an X-ray high voltage device according to the first embodiment.

Next, a circuit configuration of the X-ray high voltage device 6 will be explained with reference to FIG. 2. FIG. 2 is a diagram illustrating an example of the circuit configuration of the X-ray high voltage device 6 according to the first embodiment. As illustrated in FIG. 2, the X-ray high voltage device 6 is connected to a three-phase alternating current power supply AC and to the X-ray tube 7.

Further, as illustrated in FIG. 2, the X-ray high voltage device 6 includes a diode bridge 601, a capacitor 602, an inverter circuit 603, acquiring circuitry 604, controlling circuitry 605, a choke coil 606, a primary coil 607, a core 608, a secondary coil 609, a rectifying circuit 610, and a stray capacitance 611. The acquiring circuitry 604 is an example of the acquiring circuitry. Further, the controlling circuitry 605 is an example of the controlling circuitry.

An input terminal of the diode bridge 601 is connected to the three-phase alternating current power supply AC. Further, an output terminal of the diode bridge 601 is connected to a terminal of the capacitor 602 on the higher voltage side, to a terminal of the capacitor 602 on the lower voltage side, and to the inverter circuit 603. The diode bridge 601 applies either a full-wave rectification or a half-wave rectification to the three-phase alternating current supplied from the three-phase alternating current power supply AC and supplies the rectified result to the capacitor 602. In this manner, the capacitor 602 stores an electric charge therein and supplies a direct current to the inverter circuit 603.

The inverter circuit 603 includes a plurality of switching elements. For example, as illustrated in FIG. 2, the inverter circuit 603 includes a switching element 1S, a switching element 2S, a switching element 3S, and a switching element 4S. In this situation, the switching elements 1S, 2S, 3S, and 4S are, for example, each configured by using a low loss material such as silicon carbide (SiC) and are switched on and off by the controlling circuitry 605.

Further, as illustrated in FIG. 2, the inverter circuit 603 includes a diode 1D, a diode 2D, a diode 3D, and a diode 4D. Further, the inverter circuit 603 includes a capacitor 1C, a capacitor 2C, a capacitor 3C, and a capacitor 4C.

In this situation, FIG. 2 illustrates an example in which the switching elements 1S, 2S, 3S, and 4S are each an Insulated Gate Bipolar Transistor (IGBT); however, possible embodiments are not limited to this example. For instance, the switching elements 1S, 2S, 3S, and 4S each may be a Field-Effect Transistor (FET). In that situation, parasitic diodes included in the Field-Effect Transistors may replace the diodes 1D, 2D, 3D, and 4D.

A high voltage transformer (a transformer) including the choke coil 606, the primary coil 607, the core 608, and the secondary coil 609 is configured to raise the level of the voltage supplied from the inverter circuit 603 and to output the increased voltage to the rectifying circuit 610. Although FIG. 2 illustrates the circuit configuration including the choke coil 606, it is also acceptable to use a leakage inductance of the high voltage transformer in place of the choke coil 606. The rectifying circuit 610 is configured to rectify the alternating current of which the level of the voltage was raised by the high voltage transformer and to supply the rectified alternating current to the X-ray tube 7.

The stray capacitance 611 is a capacitance that is present due to the structure of the X-ray high voltage device 6 and is configured to substantially function as a capacitor. For example, the stray capacitance 611 is caused by windings of the high voltage transformer. In other words, because the windings include a plurality of sets made up of various types of metal that are positioned adjacent to each other in an electrically-insulated state, the windings may function as a capacitor in some situations. Further, for example, the stray capacitance 611 may be caused by resin, electrically-insulating oil, and/or the like that are present in the surroundings of the circuit (the high voltage circuit) to which the high voltage of which the level was raised by the high voltage transformer is supplied. Further, for example, the stray capacitance 611 is caused by resin, electrically-insulating oil, and/or the like with which the spaces between the windings of the high voltage transformer are filled. In other words, the resin, the electrically-insulating oil, and the like may function as a capacitor in some situations, because the dielectric constant thereof is high.

Incidentally, the higher the voltage increasing ratio of the high voltage transformer is, the larger is the impact of the stray capacitance 611 made on the inverter circuit 603. In other words, the stray capacitance 611 that is present due to the structure of the secondary side (the high voltage circuit) of the high voltage transformer makes an impact on the primary side with a magnitude multiplied by the squared value of the voltage increasing ratio. For example, when the voltage increasing ratio is "1:90", the stray capacitance 611 of "100 pF" is converted for the inverter circuit 603 as a capacitance of "(100×90×90) pF". As explained herein, the stray capacitance 611 has a large impact on the X-ray high voltage device 6, which raises the level of the voltage significantly.

An example of the configuration of the X-ray CT apparatus 1 has thus been explained. The X-ray CT apparatus 1 according to the first embodiment structured as described above is configured to reduce switching losses both when the load is large and when the load is small, with processes performed by the acquiring circuitry 604 and the controlling circuitry 605 explained in detail below. More specifically, the X-ray CT apparatus 1 is configured to acquire information about an inverter current flowing through the inverter circuit 603 and to reduce the switching losses both when the load is large and when the load is small, by implementing the zero current switching control at a first point in time at which the inverter current is substantially 0 and implementing zero voltage switching control at a second point in time excluding the first point in time. In the following sections, processes performed by the X-ray CT apparatus 1 according to the first embodiment will be explained in detail.

First, the controlling circuitry 605 acquires a targeted voltage level from the processing circuitry 34. For example, the controlling circuitry 605 acquires a setting value of the voltage to be supplied to the X-ray tube 7. Subsequently, the controlling circuitry 605 performs a switching process at a high frequency on the switching elements 1S, 2S, 3S, and 4S so that the output voltage to the X-ray tube 7 is equal to the setting value and thus switches the inverter circuit 603 on and off. For example, the controlling circuitry 605 switches the inverter circuit 603 on and off by exercising phase shift control.

Next, the phase shift control exercised by the controlling circuitry 605 will be explained with reference to FIG. 3. FIG. 3 is a chart for explaining the phase shift control according to the first embodiment. With respect to a control signal for the switching element 1S, a control signal for the switching element 2S, a control signal for the switching element 3S, and a control signal for the switching element 4S, FIG. 3 illustrates waveforms of the control signals supplied to the switching elements at different times, while the horizontal axis expresses time. In the waveforms illustrated in FIG. 3, each of the switching elements is on during the time periods between the time when the supplied control signal rises and the time when the supplied control signal falls.

First, as illustrated in FIG. 3, the controlling circuitry 605 supplies a control signal to each of the switching elements 1S, 2S, 3S, and 4S. As illustrated in FIG. 3, for the control signals supplied to the switching elements, the length of the ON time period, the length of the OFF time period, and the cycle are fixed, while the phases thereof are staggered.

Due to the control signals illustrated in FIG. 3, the inverter circuit 603 repeatedly goes through eight operation modes. More specifically, the inverter circuit 603 operates while switching between the modes, namely, an operation mode M1, an operation mode M2, an operation mode M3, an operation mode M4, an operation mode M5, an operation mode M6, an operation mode M7, and an operation mode M8, in the stated order.

In the operation mode M1, the switching element 1S and the switching element 4S are on. Accordingly, the electric charge stored in the capacitor 602 flows, as an inverter current, in a path including the switching element 1S, the choke coil 606, the primary coil 607, and the switching element 4S. In other words, in the operation mode M1, the inverter circuit 603 is on. On the contrary, the inverter circuit 603 is off, in the operation mode M2 in which only the switching element 4S is on, in the operation mode M3 in which the switching element 2S and the switching element 4S are on, and in the operation mode M4 in which only the switching element 2S is on.

In the operation mode M5, the switching element 2S and the switching element 3S are on. Accordingly, the electric charge stored in the capacitor 602 flows, as an inverter current, in a path including the switching element 2S, the choke coil 606, the primary coil 607, and the switching element 3S. In other words, in the operation mode M5, the inverter circuit 603 is on. The inverter current in the operation mode M5 flows in the opposite direction of the inverter current flowing in the operation mode M1. On the contrary, the inverter circuit 603 is off, in the operation mode M6 in which only the switching element 3S is on, in the operation mode M7 in which the switching element 1S and the switching element 3S are on, and in the operation mode M8 in which only the switching element 1S is on.

As explained above, by exercising the phase shift control, the controlling circuitry 605 switches the inverter circuit 603 on and off. Further, by varying the staggering amount of the phases, the controlling circuitry 605 is able to change the ON time periods of the inverter circuit 603 and to control the output voltage.

Further, the acquiring circuitry 604 is configured to acquire the information about the inverter current flowing through the inverter circuit 603. For example, as the information about the inverter current, the acquiring circuitry 604 acquires an inverter current value A1 indicated by the ammeter illustrated in FIG. 2.

Figure 4A:
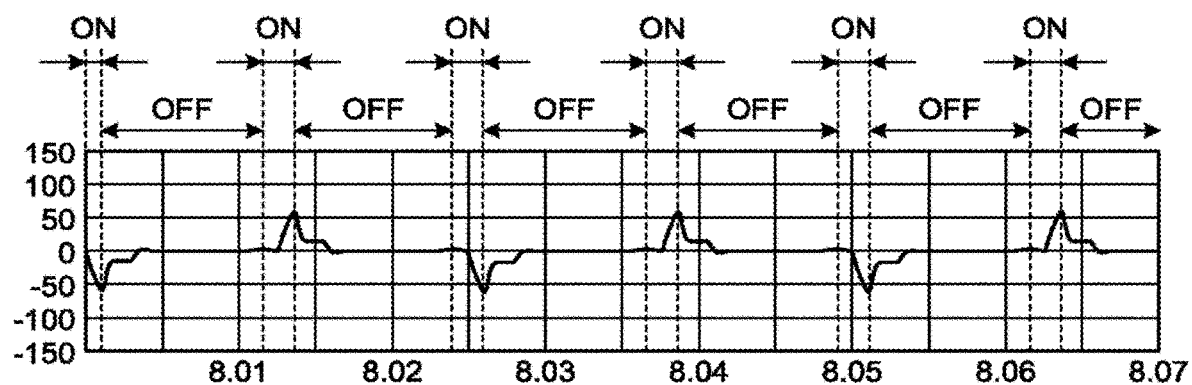
FIG. 4A is a chart illustrating an example of a current waveform of an inverter circuit according to the first embodiment.
Figure 4B:
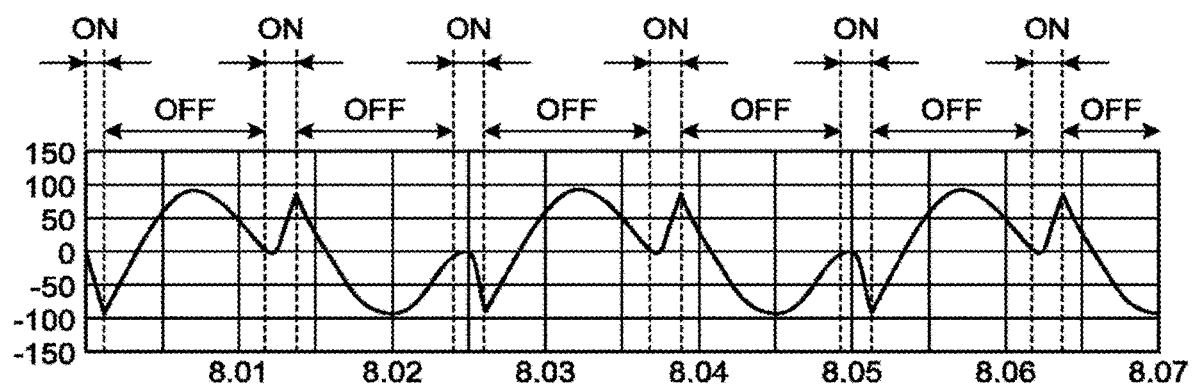
FIG. 4B is a chart illustrating another example of the current waveform of the inverter circuit according to the first embodiment.

Next, a current waveform of the inverter current value A1 exhibited while the load is small will be explained with reference to FIGS. 4A and 4B. FIGS. 4A and 4B are charts illustrating examples of the current waveform of the inverter circuit 603 according to the first embodiment. In FIGS. 4A and 4B, the horizontal axis expresses time, whereas the vertical axis expresses the inverter current value A1. Further, FIG. 4A illustrates a current waveform on the assumption that the stray capacitance 611 illustrated in FIG. 2 is absent. FIG. 4B illustrates a current waveform taking the stray capacitance 611 into account.

As illustrated in FIG. 4A, when the stray capacitance 611 is absent, a current flows while the inverter circuit 603 is on, whereas the inverter current value A1 is substantially 0 while the inverter circuit 603 is off. On the contrary, when the stray capacitance 611 is included in the circuit configuration of the X-ray high voltage device 6, a current resonance occurs between the stray capacitance 611 and the choke coil 606 as illustrated in FIG. 4B. In particular, while the inverter circuit 603 is off, the waveform exhibits a sinusoidal shape.

As illustrated in FIG. 4B, by using the stray capacitance 611, it is possible to cause the inverter current to have a current resonance. In other words, the X-ray high voltage device 6 having the circuit configuration illustrated in FIG. 2 does not require an additional resonant capacitor to cause the current resonance. Further, on the basis of the information about the inverter current acquired by the acquiring circuitry 604, the controlling circuitry 605 is able to determine a first point in time T1 at which the inverter current becomes substantially 0 and to implement the zero current switching control.

Next, the control exercised by the controlling circuitry 605 to switch on and off the switching elements 1S, 2S, 3S, and 4S while implementing the zero current switching control will be explained, with reference to FIG. 5. FIG. 5 is a drawing for explaining the zero current switching control according to the first embodiment.

First, on the basis of the inverter current value A1 acquired by the acquiring circuitry 604, the controlling circuitry 605 determines a point in time T11 at which the inverter current becomes substantially 0 and turns on the switching element 1S. Further, on the basis of the inverter current value A1 acquired by the acquiring circuitry 604, the controlling circuitry 605 determines a point in time T12 at which the inverter current becomes substantially 0 and turns on the switching element 4S. Accordingly, the switching element 1S and the switching element 4S are on, and the inverter circuit 603 is on. Subsequently, the controlling circuitry 605 turns off the switching element 1S and turns off the inverter circuit 603.

Subsequently, on the basis of the inverter current value A1 acquired by the acquiring circuitry 604, the controlling circuitry 605 determines a point in time T13 at which the inverter current becomes substantially 0 and turns on the switching element 2S. Further, on the basis of the inverter current value A1 acquired by the acquiring circuitry 604, the controlling circuitry 605 determines a point in time T14 at which the inverter current becomes substantially 0 and turns on the switching element 3S. Accordingly, the switching element 2S and the switching element 3S are on, and the inverter circuit 603 is on. After that, the controlling circuitry 605 turns off the switching element 2S and turns off the inverter circuit 603.

The points in time T11, T12, T13, and T14 illustrated in FIG. 5 are examples of the first point in time T1. The controlling circuitry 605 may perform the switching process while using the moment at which the inverter current value A1 acquired by the acquiring circuitry 604 becomes 0 as the first point in time T1. Alternatively, the controlling circuitry 605 may perform the switching process by calculating the time at which the inverter current becomes substantially 0 on the basis of a change amount per unit time period or the like in the inverter current value A1 acquired by the acquiring circuitry 604 and further using the calculated time as the first point in time T1.

As explained above, the controlling circuitry 605 reduces the switching losses by exercising control so as to perform the switching process at the first point in time T1 at which the inverter current becomes substantially 0. In other words, at the first point in time T1, the controlling circuitry 605 reduces the switching losses exhibited while the load is small, by implementing the zero current switching control on the switching elements 1S, 2S, 3S, and 4S.

Incidentally, as for the current resonance using the stray capacitance 611, the resonant frequency may not have a fixed value in some situations. For example, in some situations, the resonant frequency may fluctuate in correspondence with the stray capacitance 611, which changes depending on the dielectric constant of the resin, the structure of the X-ray high voltage device 6, and the like. Even in those situations, because the controlling circuitry 605 determines the first point in time T1 on the basis of the information about the inverter current acquired by the acquiring circuitry 604, the controlling circuitry 605 is able to reduce the switching losses by turning on the inverter circuit 603 while the inverter current is in the state of being substantially 0.

Figure 6A:
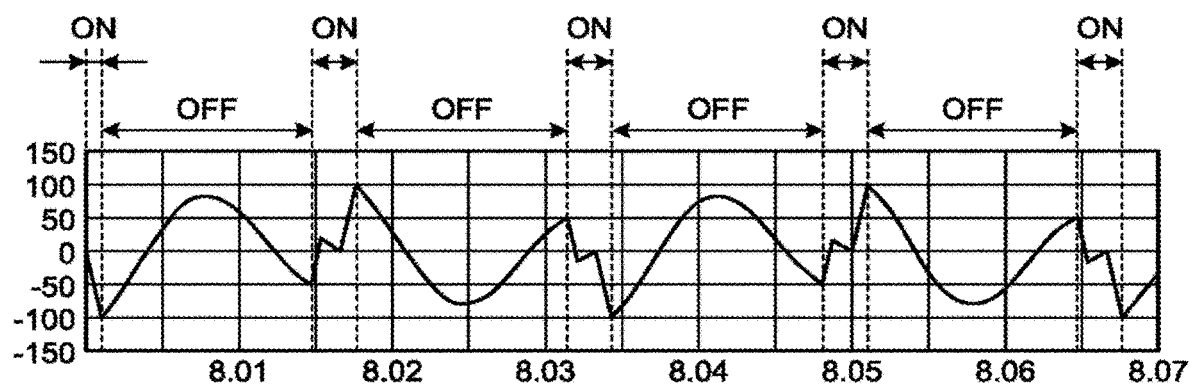
FIG. 6A is a chart illustrating yet another example of the current waveform of the inverter circuit according to the first embodiment.
Figure 6B:
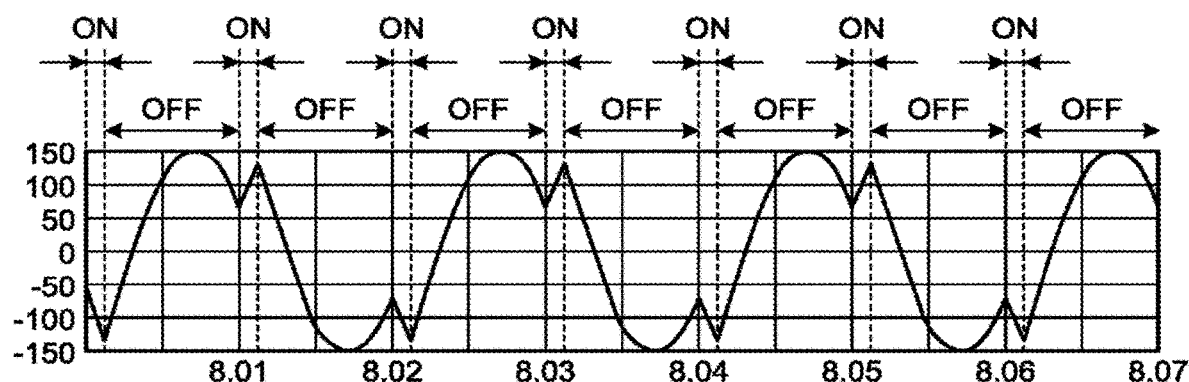
FIG. 6B is a chart illustrating yet another example of the current waveform of the inverter circuit according to the first embodiment.

In this situation, as another method for implementing the zero current switching control, it may also be possible, for example, to perform a switching process by using a constant cycle corresponding to the resonant frequency. However, because the resonant frequency fluctuates, the timing with which the inverter current becomes substantially 0 also changes. Accordingly, when the switching process is simply performed by using a constant cycle, it is expected that a switching loss may occur, when the inverter circuit 603 is turned on after the current exceeds the zero point as illustrated in FIG. 6A, or when the inverter circuit 603 is turned on before the current reaches the zero point as illustrated in FIG. 6B. FIGS. 6A and 6B are charts illustrating other examples of the current waveform of the inverter circuit 603 according to the first embodiment.

Figure 7A:
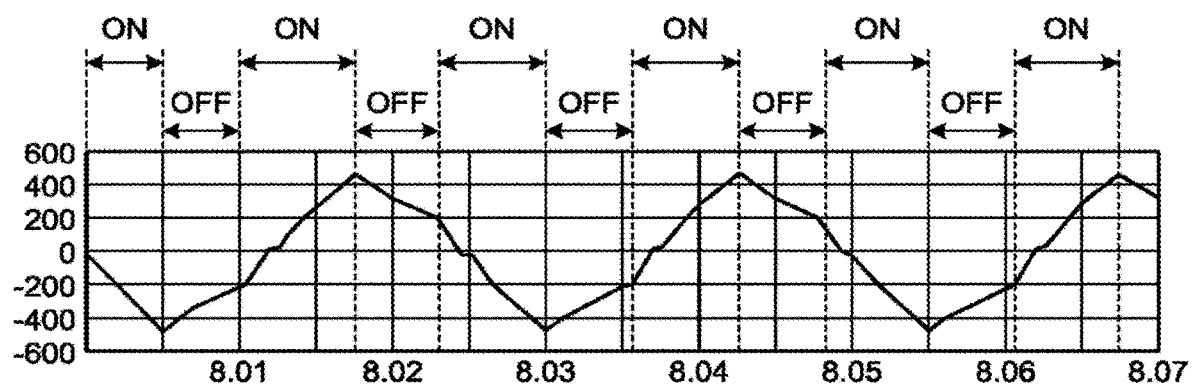
FIG. 7A is a chart illustrating yet another example of the current waveform of the inverter circuit according to the first embodiment.
Figure 7B:
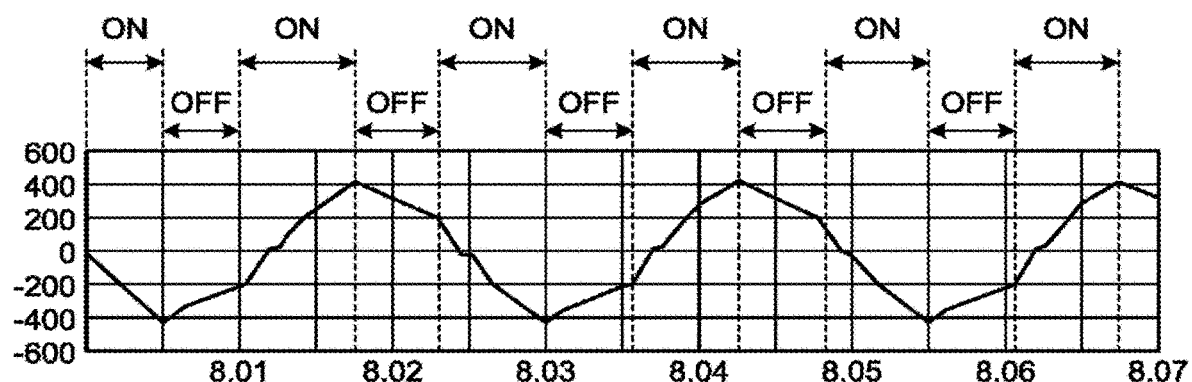
FIG. 7B is a chart illustrating yet another example of the current waveform of the inverter circuit according to the first embodiment.

Next, a current waveform of the inverter current value A1 exhibited while the load is large will be explained with reference to FIGS. 7A and 7B. FIGS. 7A and 7B are charts illustrating other examples of the current waveform of the inverter circuit 603 according to the first embodiment. In FIGS. 7A and 7B, the horizontal axis expresses time, whereas the vertical axis expresses the inverter current value A1. FIG. 7A illustrates a current waveform on the assumption that the stray capacitance 611 illustrated in FIG. 2 is absent. FIG. 7B illustrates a current waveform taking the stray capacitance 611 into account.

As illustrated in FIGS. 7A and 7B, when the load is large, the time periods during which the inverter circuit 603 is off are shorter than those exhibited when the load is small. Further, as illustrated in FIGS. 7A and 7B, when the load is large, the impact of the stray capacitance 611 does not appear so much in the current waveforms. Accordingly, the current waveforms are similar regardless of whether the stray capacitance 611 is present or absent. For this reason, when the load is large, in some situations, the controlling circuitry 605 may not be able to determine the first point in time T1 at which the inverter current becomes substantially 0, while the inverter circuit 603 is off. In those situations, the controlling circuitry 605 is not able to implement the zero current switching control.

In those situations, the controlling circuitry 605 may be able to determine the first point in time T1 at which the inverter current becomes substantially 0, by arranging the OFF time periods to be longer. However, arranging the OFF time periods to be longer would lead to a decrease in the switching frequency, and disadvantages might occur where the output voltage ripples or the size of the coils needs to be larger.

To cope with these situations, when being unable to determine the first point in time T1, the controlling circuitry 605 exercises control by implementing the zero voltage switching control. In other words, at a second point in time T2 excluding the first point in time T1, the controlling circuitry 605 exercises control by implementing the zero voltage switching control on the switching elements 1S, 2S, 3S, and 4S.

In the following sections, the zero voltage switching control implemented by the controlling circuitry 605 will be explained. First, a circuit configuration of the X-ray high voltage device 6 on which it is possible to implement the zero voltage switching control will be explained, with reference back to FIG. 2.

As illustrated in FIG. 2, the inverter circuit 603 includes the plurality of switching elements (the switching elements 1S, 2S, 3S, and 4S) that can be switched on and off by the controlling circuitry 605. Further, the inverter circuit 603 includes the plurality of diodes (the diodes 1D, 2D, 3D, and 4D). Further, the inverter circuit 603 includes the plurality of capacitors (the capacitors 1C, 2C, 3C, and 4C).

In the following sections, in the inverter circuit 603, the part including the switching element 1S, the diode 1D, the capacitor 1C, the switching element 2S, the diode 2D, and the capacitor 2C may be referred to as a first arm. In contrast, in the inverter circuit 603, the part including the switching element 3S, the diode 3D, the capacitor 3C, the switching element 4S, the diode 4D, and the capacitor 4C may be referred to as a second arm.

When the phase shift control illustrated in FIG. 3 is exercised, the time periods during which the switching element 1S is on and the time periods during which the switching element 2S is on have an advanced phase compared to the time periods during which the inverter circuit 603 is on (e.g., in the operation mode M1 or the operation mode M5). The first arm, which includes the switching elements 1S and 2S mentioned herein, may be referred to as an advanced arm. In contrast, the time period during which the switching element 3S is on and the time periods during which the switching element 4S is on have a delayed phase compared to the time periods during which the inverter circuit 603 is on. The second arm, which includes the switching elements 3S and 4S mentioned herein, may be referred to as a delayed arm.

The electrostatic capacitance of the capacitor 1C is set in such a manner that the voltage between the collector and the emitter (hereinafter, "collector-emitter voltage") of the capacitor 1C becomes zero when a dead time of the first arm ends. The electrostatic capacitance of the capacitor 2C is set in such a manner that the collector-emitter voltage of the capacitor 2C becomes zero when a dead time of the first arm ends. The electrostatic capacitance of the capacitor 3C is set in such a manner that the collector-emitter voltage of the capacitor 3C becomes zero when a dead time of the second arm ends. The electrostatic capacitance of the capacitor 4C is set in such a manner that the collector-emitter voltage of the capacitor 4C becomes zero when a dead time of the second arm ends.

In this situation, the dead time is a time period provided immediately before each of the switching elements is turned on, so that the two switching elements included in each of the arms do not get turned on at the same time as each other. The dead time of the first arm is determined on the basis of the time period required by turning off the switching element 1S and the time period required by turning off the switching element 2S, the switching elements 1S and 2S being included in the first arm. Further, the dead time of the second arm is determined on the basis of the time period required by turning off the switching element 4S and the time period required by turning off the switching element 3S, the switching elements 4S and 3S being included in the second arm.

Further, as illustrated in FIG. 2, the emitter of the switching element 1S and the collector of the switching element 2S are connected to one of the terminals of the choke coil 606. In other words, the switching element 2S is connected in series to the switching element 1S. Further, the collector of the switching element 1S is connected to one of the terminals of the capacitor 602 positioned on the higher voltage side. Further, the emitter of the switching element 2S is connected to one of the terminals of the capacitor 602 positioned on the lower voltage side.

The cathode of the diode 1D is connected to the collector of the switching element 1S. Further, the anode of the diode 1D is connected to the emitter of the switching element 1S. In other words, the diode 1D is connected in parallel to the switching element 1S.

The capacitor 1C is connected in parallel to the switching element 1S. For example, one of the terminals of the capacitor 1C is connected to the collector of the switching element 1S. Further, the other terminal of the capacitor 1C is connected to the emitter of the switching element 1S.

One of the terminals of the choke coil 606 is connected to the other terminal of the capacitor 1C. As a result, when viewed from the switching element 1S, the capacitor 1C and the choke coil 606 are connected in parallel to each other. For this reason, a parallel resonance is caused by the capacitor 1C and the choke coil 606 as explained later.

The cathode of the diode 2D is connected to the collector of the switching element 2S. The anode of the diode 2D is connected to the emitter of the switching element 2S. In other words, the diode 2D is connected in parallel to the switching element 2S.

The capacitor 2C is connected in parallel to the switching element 2S. For example, one of the terminals of the capacitor 2C is connected to the collector of the switching element 2S. Further, the other terminal of the capacitor 2C is connected to the emitter of the switching element 2S.

One of the terminals of the choke coil 606 is connected to the one of the terminals of the capacitor 2C. As a result, when viewed from the switching element 2S, the capacitor 2C and the choke coil 606 are connected in parallel to each other. For this reason, a parallel resonance is caused by the capacitor 2C and the choke coil 606 as explained later.

The emitter of the switching element 3S and the collector of the switching element 4S are connected to the other terminal of the primary coil 607. In other words, the switching element 4S is connected in series to the switching element 3S. The collector of the switching element 3S is connected to the one of the terminals of the capacitor 602 positioned on the higher voltage side. The emitter of the switching element 4S is connected to the one of the terminals of the capacitor 602 positioned on the lower voltage side. In other words, the second arm is connected in parallel to the first arm.

The cathode of the diode 3D is connected to the collector of the switching element 3S. The anode of the diode 3D is connected to the emitter of the switching element 3S. In other words, the diode 3D is connected in parallel to the switching element 3S.

The capacitor 3C is connected in parallel to the switching element 3S. For example, one of the terminals of the capacitor 3C is connected to the collector of the switching element 3S. Further, the other terminal of the capacitor 3C is connected to the emitter of the switching element 3S.

The other terminal of the choke coil 606 is connected to the other terminal of the capacitor 3C via the primary coil 607. As a result, when viewed from the switching element 3S, the capacitor 3C and the choke coil 606 are connected in parallel to each other. For this reason, a parallel resonance is caused by the capacitor 3C and the choke coil 606 as explained later.

The cathode of the diode 4D is connected to the collector of the switching element 4S. The anode of the diode 4D is connected to the emitter of the switching element 4S. In other words, the diode 4D is connected in parallel to the switching element 4S.

The capacitor 4C is connected in parallel to the switching element 4S. For example, one of the terminals of the capacitor 4C is connected to the collector of the switching element 4S. Further, the other terminal of the capacitor 4C is connected to the emitter of the switching element 4S.

The other terminal of the choke coil 606 is connected to the one of the terminals of the capacitor 4C via the primary coil 607. As a result, as viewed from the switching element 4S, the capacitor 4C and the choke coil 606 are connected in parallel to each other. For this reason, a parallel resonance is caused by the capacitor 4C and the choke coil 606 as explained later.

The controlling circuitry 605 is connected to the gates and the emitters of the switching element 1S, the switching element 2S, the switching element 4S, and the switching element 3S and is configured to switch the switching elements on and off.

A circuit configuration of the X-ray high voltage device 6 has thus been explained. In the circuit configuration as described above, the controlling circuitry 605 is configured to implement the zero voltage switching control. In the following sections, the zero voltage switching control implemented by the controlling circuitry 605 will be explained, with reference to FIG. 8. FIG. 8 is a chart for explaining the zero voltage switching control according to the first embodiment. With respect to control signals for the switching elements 1S and 2S included in the first arm and control signals for the switching elements 3S and 4S included in the second arm, FIG. 8 illustrates waveforms of the control signals supplied to the switching elements at different times, while the horizontal axis expresses time. In the waveforms illustrated in FIG. 8, each of the switching elements is on during the time periods between the time when the supplied control signal rises and the time when the supplied control signal falls.

As illustrated in FIG. 8, the controlling circuitry 605 sends a control signal to each of the switching elements 1S, 2S, 3S, and 4S. Further, the controlling circuitry 605 exercises control so that the inverter circuit 603 repeats the eight operation modes, namely, the operation modes M1, M2, M3, M4, M5, M6, M7, and M8.

First, in the operation mode M1, the switching elements 1S and 4S are on. Accordingly, the electric charge stored in the capacitor 602 flows, as an inverter current, in a path including the switching element 1S, the choke coil 606, the primary coil 607, and the switching element 4S. In other words, in the operation mode M1, the inverter circuit 603 is on. As a result, the inverter circuit 603 supplies a current to the choke coil 606 and to the primary coil 607. In this situation, the choke coil 606 stores energy therein by using the current supplied thereto from the inverter circuit 603.

Subsequently, the controlling circuitry 605 switches the switching element 1S off and switches the operation mode into the operation mode M2. At this time, the capacitor 1C has been discharged and the collector-emitter voltage of the switching element 1S is zero. Accordingly, the controlling circuitry 605 is able to implement the zero voltage switching control on the switching element 1S.

In the operation mode M2, the first arm including the switching element 1S and the switching element 2S is in a dead time. In contrast, the second arm including the switching element 3S and the switching element 4S is in a reflux mode in the operation mode M2. As a result, the capacitor 1C is charged, and the capacitor 2C is discharged. In this situation, the sum of the voltage of the capacitor 1C and the voltage of the capacitor 2C is always equal to the voltage of the capacitor 602.

Further, in the operation mode M2, the capacitor 602 causes a current to flow in a path including the capacitor 1C, the choke coil 606, the primary coil 607, and the switching element 4S. Due to this current, the capacitor 1C is charged, and the collector-emitter voltage of the switching element 1S increases.

Further, in the operation mode M2, the choke coil 606 causes a current to flow in a path including the primary coil 607, the switching element 4S, and the capacitor 2C. This current has been generated by the energy stored in the choke coil 606 in the operation mode M1 and the parallel resonance between the capacitor 2C and the choke coil 606. Due to this current, the capacitor 2C is discharged, and the collector-emitter voltage of the switching element 2S decreases.

Further, in the operation mode M2, even after the capacitor 1C completes being charged and the capacitor 2C completes being discharged, the choke coil 606 keeps causing a current to flow in a path including the primary coil 607, the switching element 4S, and the diode 2D. This current has been generated by the energy stored in the choke coil 606 in the operation mode M1.

Subsequently, the controlling circuitry 605 switches the switching element 2S on and switches the operation mode into the operation mode M3. At this time, the capacitor 2C has been discharged, and the diode 2D is in a conducting state. Accordingly, at this time, the collector-emitter voltage of the switching element 2S is zero, and the controlling circuitry 605 is able to implement the zero voltage switching control on the switching element 2S.

The first arm is in a reflux mode in the operation mode M3. The second arm is also in the reflux mode, as continued from in the operation mode M2. In the reflux mode, the choke coil 606 causes a current to flow in the path including the primary coil 607, the switching element 4S, and the switching element 2S. This current has been generated by the energy stored in the choke coil 606 in the operation mode M1.

Subsequently, the controlling circuitry 605 switches the switching element 4S off and switches the operation mode into the operation mode M4. At this time, the capacitor 4C has been discharged, and the collector-emitter voltage of the switching element 4S is zero. Accordingly, the controlling circuitry 605 is able to implement the zero voltage switching control on the switching element 4S.

In the operation mode M4, the first arm is in the reflux mode, as continued from in the operation mode M3. Accordingly, the capacitor 4C is charged, and the capacitor 3C is discharged. In this situation, the sum of the voltage of the capacitor 3C and the voltage of the capacitor 4C is always equal to the voltage of the capacitor 602. In contrast, the second arm is in a dead time in the operation mode M4.

In the operation mode M4, the choke coil 606 causes a current to flow in the path including the primary coil 607, the capacitor 4C, and the switching element 2S. This current has been generated by the energy stored in the choke coil 606 in the operation mode M1. Due to this current, the capacitor 4C is charged, and the collector-emitter voltage of the switching element 4S increases.

Further, in the operation mode M4, the choke coil 606 causes a current to flow in a path including the capacitor 3C, the capacitor 602, and the switching element 2S. This current has been generated by the energy stored in the choke coil 606 in the operation mode M1 and the parallel resonance between the capacitor 3C and the choke coil 606. Due to this current, the capacitor 3C is discharged, and the collector-emitter voltage of the switching element 3S decreases.

In the operation mode M4, even after the capacitor 4C completes being charged and the capacitor 3C completes being discharged, the choke coil 606 keeps causing a current to flow in a path including the primary coil 607, the diode 3D, the capacitor 602, and the switching element 2S. This current has been generated by the energy stored in the choke coil 606 in the operation mode M1.

Subsequently, the controlling circuitry 605 switches the switching element 3S on and switches the operation mode into the operation mode M5. At this time, the capacitor 3C has been discharged, and the diode 3D is in a conducting state. Accordingly, at this time, the collector-emitter voltage of the switching element 3S is zero, and the controlling circuitry 605 is able to implement the zero voltage switching control on the switching element 3S.

In the operation mode M5, the switching elements 2S and 3S are on. Accordingly, the electric charge stored in the capacitor 602 flows, as an inverter current, in a path including the switching element 3S, the primary coil 607, the choke coil 606, and the switching element 2S. In other words, in the operation mode M5, the inverter circuit 603 is on. As a result, the inverter circuit 603 supplies a current to the choke coil 606 and to the primary coil 607. In this situation, the choke coil 606 stores energy therein by using the current supplied thereto from the inverter circuit 603.

Subsequently, the controlling circuitry 605 switches the switching element 2S off and switches the operation mode into the operation mode M6. At this time, the capacitor 2C has been discharged, and the collector-emitter voltage of the switching element 2S is zero. Accordingly, the controlling circuitry 605 is able to implement the zero voltage switching control on the switching element 2S.

In the operation mode M6, the first arm is in a dead time, whereas the second arm is in a reflux mode. Due to the reflux mode, the capacitor 2C is charged, whereas the capacitor 1C is discharged. In this situation, the sum of the voltage of the capacitor 1C and the voltage of the capacitor 2C is always equal to the voltage of the capacitor 602.

Further, in the operation mode M6, the capacitor 602 causes a current to flow in a path including the switching element 3S, the primary coil 607, the choke coil 606, and the capacitor 2C. Due to this current, the capacitor 2C is charged, and the collector-emitter voltage of the switching element 2S increases.

Further, in the operation mode M6, the choke coil 606 causes a current to flow in a path including the capacitor 1C, the switching element 3S, and the primary coil 607. This current has been generated by the energy stored in the choke coil 606 in the operation mode M5 and the parallel resonance between the capacitor 1C and the choke coil 606. Due to this current, the capacitor 1C is discharged, and the collector-emitter voltage of the switching element 1S decreases.

Further, in the operation mode M6, even after the capacitor 2C completes being charged and the capacitor 1C completes being discharged, the choke coil 606 keeps causing a current to flow in a path including the diode 1D, the switching element 3S, and the primary coil 607. This current has been generated by the energy stored in the choke coil 606 in the operation mode M5.

Subsequently, the controlling circuitry 605 switches the switching element 1S on and switches the operation mode into the operation mode M7. At this time, the capacitor 1C has been discharged, and the diode 1D is in a conducting state. Accordingly, at this time, the collector-emitter voltage of the switching element 1S is zero, and the controlling circuitry 605 is able to implement the zero voltage switching control on the switching element 1S.

In the operation mode M7, the first arm is in a reflux mode. The second arm is also in the reflux mode, as continued from in the operation mode M6. In the reflux mode, the choke coil 606 causes a current to flow in a path including the switching element 1S, the switching element 3S, and the primary coil 607. This current has been generated by the energy stored in the choke coil 606 in the operation mode M5.

Subsequently, the controlling circuitry 605 switches the switching element 3S off and switches the operation mode into the operation mode M8. At this time, the capacitor 3C has been discharged, and the collector-emitter voltage of the switching element 3S is zero. Accordingly, the controlling circuitry 605 is able to implement the zero voltage switching control on the switching element 3S.

In the operation mode M8, the first arm is in a reflux mode. As a result, the capacitor 3C is charged, and the capacitor 4C is discharged. In this situation, the sum of the voltage of the capacitor 3C and the voltage of the capacitor 4C is always equal to the voltage of the capacitor 602. In contrast, the second arm is in a dead time in the operation mode M8.

In the operation mode M8, the choke coil 606 causes a current to flow in a path including the switching element 1S, the capacitor 3C, and the primary coil 607. This current has been generated by the energy stored in the choke coil 606 in the operation mode M5. Due to this current, the capacitor 3C is charged, and the collector-emitter voltage of the switching element 3S increases.

Further, in the operation mode M8, the choke coil 606 causes a current to flow in a path including the switching element 1S, the capacitor 602, the capacitor 4C, and the primary coil 607. This current has been generated by the energy stored in the choke coil 606 in the operation mode M5 and the parallel resonance between the capacitor 4C and the choke coil 606. Due to this current, the capacitor 4C is discharged, and the collector-emitter voltage of the switching element 4S decreases.

Further, in the operation mode M8, even after the capacitor 3C completes being charged and the capacitor 4C completes being discharged, the choke coil 606 keeps causing a current to flow in a path including the switching element 1S, and the capacitor 602, the diode 4D, and the primary coil 607. This current has been generated by the energy stored in the choke coil 606 in the operation mode M5.

Subsequently, the controlling circuitry 605 switches the switching element 4S on and switches the operation mode into the operation mode M1. At this time, the capacitor 4C has been discharged, and the diode 4D is in a conducting state. Accordingly, at this time, the collector-emitter voltage of the switching element 4S is zero, and the controlling circuitry 605 is able to implement the zero voltage switching control on the switching element 4S. Further, the controlling circuitry 605 controls the switching elements so as to repeat the abovementioned eight operation modes, namely, the operation modes M1, M2, M3, M4, M5, M6, M7, and M8.

As explained above, the controlling circuitry 605 implements the zero voltage switching control by performing the phase shift control, by making use of the parallel resonance occurring between the resonant capacitors (the capacitor 1C, the capacitor 2C, the capacitor 3C, and the capacitor 4C) each connected in parallel to a corresponding one of the switching elements and the choke coil 606. In other words, the controlling circuitry 605 realizes the zero voltage switching control by extracting the electric charge held in the resonant capacitor connected in parallel to the switching element, while making use of the energy stored in the choke coil 606, during the dead time provided immediately before the switching element is turned on.

In this situation, the voltage levels of the switching elements exhibited while the controlling circuitry 605 is implementing the zero voltage switching control will be explained, with reference to FIG. 9. FIG. 9 is a chart illustrating examples of control signals and voltage levels of switching elements according to the first embodiment. For the sake of convenience in the explanation, FIG. 9 illustrates only the control signals and the voltage levels of the switching elements in the first arm (i.e., the switching elements 1S and 2S). With respect to the control signals for the switching elements 1S and 2S, the first and the third sections of FIG. 9 illustrate waveforms of the control signals supplied to the switching elements at different times, while the horizontal axis expresses time. In the waveforms illustrated in FIG. 9, each of the switching elements is on during the time periods between the time when the supplied control signal rises and the time when the supplied control signal falls. Further, with respect to the collector-emitter voltage levels of the switching elements 1S and 2S, the second and the fourth sections of FIG. 9 illustrate the levels of voltage applied to between the collector and the emitter of the respective switching elements at different times, while the horizontal axis expresses time.

First, in the operation mode M1 in which the inverter circuit 603 is on, the controlling circuitry 605 stores energy in the choke coil 606. Subsequently, in the operation mode M2 in which the first arm is in a dead time, the controlling circuitry 605 lowers the collector-emitter voltage of the switching element 2S by extracting the electric charge from the capacitor 2C by using the energy stored in the choke coil 606. After that, by turning on the switching element 2S in the state where the collector-emitter voltage is substantially 0, the controlling circuitry 605 is able to avoid the occurrence of switching losses.

Further, in the operation mode M5 in which the inverter circuit 603 is on, the controlling circuitry 605 stores energy in the choke coil 606. Subsequently, in the operation mode M6 in which the first arm is in a dead time, the controlling circuitry 605 lowers the collector-emitter voltage of the switching element 1S by extracting the electric charge from the capacitor 1C by using the energy stored in the choke coil 606. After that, by turning on the switching element 1S in the state where the collector-emitter voltage is substantially 0, the controlling circuitry 605 is able to avoid the occurrence of switching losses.

In this situation, as explained above, what extracts the electric charge from the resonant capacitor is the energy stored in the choke coil 606. Further, what stores the energy in the choke coil 606 is the inverter current flowing through the inverter circuit 603. Accordingly, as illustrated in FIG. 10, when the inverter current is small, it may be impossible, in some situations, to extract the electric charge from the resonant capacitor until the collector-emitter voltage of the switching element becomes 0. FIG. 10 is another chart illustrating examples of control signals and voltage levels of the switching elements according to the first embodiment. With respect to the control signals for the switching elements 1S and 2S, the first and the third sections of FIG. 10 illustrate waveforms of the control signals supplied to the switching elements at different times, while the horizontal axis expresses time. In the waveforms illustrated in FIG. 10, each of the switching elements is on during the time periods between the time when the supplied control signal rises and the time when the supplied control signal falls. Further, with respect to the collector-emitter voltage levels of the switching elements 1S and 2S, the second and the fourth sections of FIG. 10 illustrate the levels of voltage applied to between the collector and the emitter of the respective switching elements at different times, while the horizontal axis expresses time.

However, the controlling circuitry 605 implements the zero voltage switching control at the second point in time T2 when the controlling circuitry 605 fails to determine the first point in time T1 due to a large load. In other words, when the controlling circuitry 605 implements the zero voltage switching control, a sufficient amount of inverter current is flowing. Thus, the controlling circuitry 605 is able to implement the zero voltage switching control after extracting the electric charge from the resonant capacitor until the collector-emitter voltage of the switching element becomes 0.

Next, an example of a procedure of processes performed by the X-ray CT apparatus 1 will be explained, with reference to FIG. 11. FIG. 11 is a flowchart for explaining a flow in a series of processes performed by the X-ray CT apparatus 1 according to the first embodiment. Step S103 is a step corresponding to the acquiring circuitry 604. Steps S101, S102, S104, S105, S106, and S107 are steps corresponding to the controlling circuitry 605.

First, the controlling circuitry 605 acquires a targeted voltage level from the processing circuitry 34 (step S101). For example, the processing circuitry 34 determines an X-ray tube voltage value to be used by the X-ray tube 7 to generate X-rays and notifies the controlling circuitry 605 of the output voltage of the X-ray high voltage device 6. Subsequently, in accordance with the targeted voltage level, the controlling circuitry 605 performs a switching process on the switching elements, namely, the switching elements 1S, 2S, 3S, and 4S (step S102) and supplies high voltage to the X-ray tube 7.

In this situation, the acquiring circuitry 604 acquires information about the inverter current flowing through the inverter circuit 603 (step S103). For example, the acquiring circuitry 604 acquires the inverter current value A1 indicated by the ammeter illustrated in FIG. 2. In this situation, on the basis of the information about the inverter current, the controlling circuitry 605 determines the first point in time T1 at which the inverter current becomes substantially 0 (step S104).

When being able to determine the first point in time T1 (step S104: Yes), the controlling circuitry 605 exercises control by implementing the zero current switching control on the switching elements, namely, the switching elements 1S, 2S, 3S, and 4S (step S105). On the contrary, when being unable to determine the first point in time T1 (step S104: No), the controlling circuitry 605 exercises control by implementing the zero voltage switching control on the switching elements, namely, the switching elements 1S, 2S, 3S, and 4S (step S106).

Further, while implementing either the zero current switching control at step S105 or the zero voltage switching control at step S106, the controlling circuitry 605 judges whether or not the high voltage will continue to be supplied to the X-ray tube 7 (step S107). When the high voltage will continue to be supplied (step S107: Yes), the controlling circuitry 605 returns to step S101 and acquires a targeted voltage level. The voltage level acquired by the controlling circuitry 605 after returning to step S101 may be different from the voltage level previously acquired. For example, the voltage level is different when control is exercised to modulate an output current while the X-ray tube 7 is outputting X-rays (an X-ray tube current modulation) during a scan performed on the patient P. In other words, the processing circuitry 34 determines the output voltage of the X-ray high voltage device 6 so as to increase the intensities of the X-rays emitted from the X-ray tube 7 in a specific X-ray tube position and so as to decrease the intensities of the X-rays emitted from the X-ray tube 7 in a range other than the specific X-ray tube position. In that situation, the voltage level acquired by the controlling circuitry 605 at step S101 varies depending on the X-ray tube position of the X-ray tube 7.

Further, for example, when control is exercised to modulate the output voltage while X-ray tube 7 is outputting X-rays during a scan performed on the patient P, the voltage level acquired by the controlling circuitry 605 after returning to step S101 may be different from the voltage level that was previously acquired. In this situation, the control to modulate the output voltage while the X-rays are being output is, for example, a Dual-Energy (DE) acquisition or a Multi-Energy (ME) acquisition that uses a fast kV switching scheme. In the dual-energy acquisition, control is exercised so that, by using X-rays having two mutually-different energy levels, pieces of projection data corresponding to the mutually-different energy levels are acquired. In contrast, in the multi-energy acquisition, control is exercised so that, by using X-rays having three or more mutually-different energy levels, pieces of projection data corresponding to the mutually-different energy levels are acquired.

In other words, when executing the dual-energy acquisition or the multi-energy acquisition by using the fast kV switching scheme, the processing circuitry 34 determines the output voltage of the X-ray high voltage device 6 so that the energy level of the X-rays varies depending on the X-ray tube position of the X-ray tube 7. In that situation, the voltage level acquired by the controlling circuitry 605 at step S101 varies depending on the X-ray tube position. In this situation, by executing the dual-energy acquisition or the multi-energy acquisition, the X-ray CT apparatus 1 acquires the pieces of projection data corresponding to the energy levels and is thus able to distinguish the types, the atomic numbers, the densities, and the like of the substances contained in the patient P, by making use of a notion that X-ray absorption characteristics are different among the substances. Further, when the high voltage will not continue to be supplied (step S107: No), the acquiring circuitry 604 and the controlling circuitry 605 ends the process.

As explained above, according to the first embodiment, the inverter circuit 603 includes the plurality of switching elements. Further, the acquiring circuitry 604 is configured to acquire the information about the inverter current flowing through the inverter circuit 603. Further, on the basis of the information about the inverter current, the controlling circuitry 605 is configured to determine the first point in time T1 at which the inverter current becomes substantially 0. At the first point in time T1, the controlling circuitry 605 implements the zero current switching control on the plurality of switching elements. At the second point in time T2 excluding the first point in time, the controlling circuitry 605 exercises control by implementing the zero voltage switching control on the plurality of switching elements. With these arrangements, the X-ray CT apparatus 1 according to the first embodiment is able to reduce the switching losses by making it possible to exercise soft switching control in all the range from when the load is small to when the load is large.

Further, according to the first embodiment, as the first points in time T1, the controlling circuitry 605 is configured to determine the times at which the inverter current resonating due to the stray capacitance 611 becomes substantially 0. Accordingly, the X-ray CT apparatus 1 according to the first embodiment is able to implement the zero current switching control by using the stray capacitance that is present in the high voltage circuit, without the need to additionally provide a resonant capacitor for causing a current resonance. Further, the X-ray CT apparatus 1 according to the first embodiment is able to exercise control while switching between the zero current switching control and the zero voltage switching control, without the need to change the circuit configuration by, for example, adding a resonant capacitor thereto.

Further, according to the first embodiment, the controlling circuitry 605 is configured to determine the first point in time T1 at which the inverter current becomes substantially 0 on the basis of the information about the inverter current and to exercise the zero current switching control. Consequently, even when the first point in time T1 at which the inverter current becomes substantially 0 changes due to the fluctuations of the stray capacitance, the X-ray CT apparatus 1 according to the first embodiment is able to implement the zero current switching control.

Further, according to the first embodiment, depending on whether or not it is possible to determine the first point in time T1, the controlling circuitry 605 selectively determines which one of the two soft switching control schemes shall be implemented, namely, the zero current switching control or the zero voltage switching control. Consequently, the X-ray CT apparatus 1 according to the first embodiment is able to select the soft switching control scheme to be implemented, without the need to monitor the voltage value or the current value of the alternating current being input.

The first embodiment has thus been explained. It is possible to carry out the present disclosure in various different forms other than those explained above in the first embodiment.

In the embodiment described above, the example is explained in which the first point in time T1 at which the inverter current becomes substantially 0 is determined, so that the zero voltage switching control is implemented at the second point in time T2 excluding the first point in time T1. In other words, the example is explained in which the zero current switching control is implemented by detecting the first point in time T1 at which the inverter current becomes substantially 0, so that the zero voltage switching control is implemented when it is impossible to detect the zero point of the inverter current. However, possible embodiments are not limited to this example.

For instance, the controlling circuitry 605 may be configured to determine which of the soft switching control schemes (namely, either the zero current switching control or the zero voltage switching control) should be implemented, depending on the load. In one example, the controlling circuitry 605 at first determines, with respect to each of various output voltage levels, an output current level serving as a boundary point between the zero current switching control and the zero voltage switching control.

Figure 12:
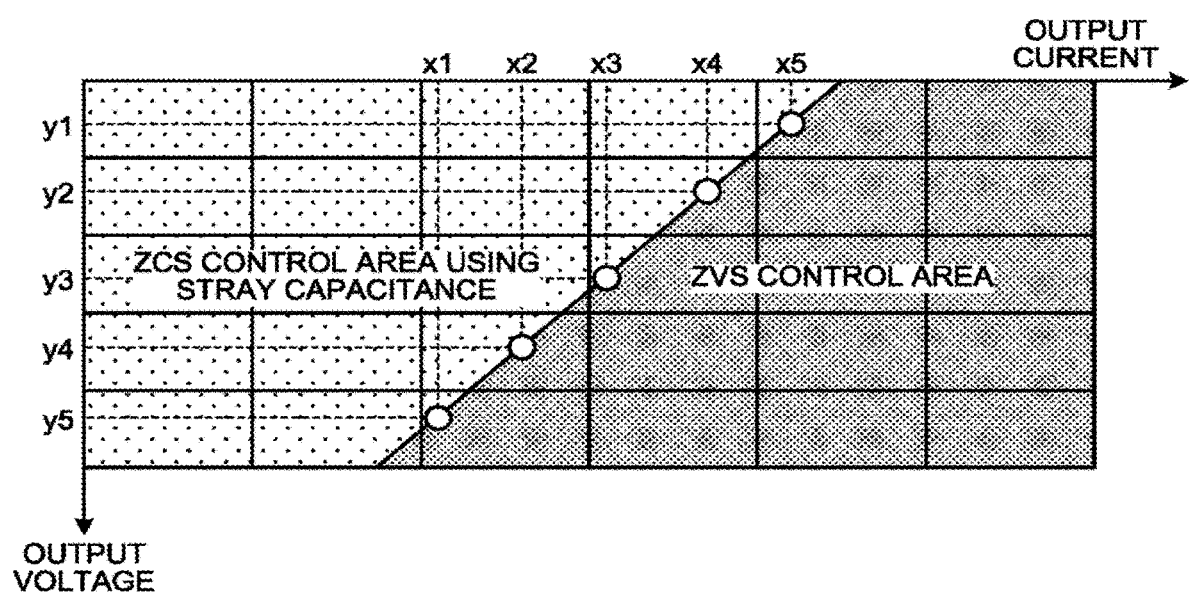
FIG. 12 is a chart illustrating an example of a method for switching between zero current switching control and zero voltage switching control according to the second embodiment.

Next, the output current level serving as the boundary point between the zero current switching control and the zero voltage switching control will be explained, with reference to FIG. 12. FIG. 12 is a chart illustrating an example of a method for switching between the zero current switching control and the zero voltage switching control according to a second embodiment. In FIG. 2, the horizontal axis expresses output current levels, whereas the vertical axis expresses output voltage levels.

For example, the controlling circuitry 605 determines that "x5" shall be used as a boundary point when the output voltage level is "y1". The controlling circuitry 605 is able to calculate such a boundary point on the basis of, for example, whether or not a switching loss occurred during zero voltage switching control implemented in the past. In one example, the controlling circuitry 605 implements the zero voltage switching control while setting the output voltage level to "y1" and gradually decreasing the output current level starting with a value larger than "x5". In the situation where a switching loss occurs at the point in time when the output current level becomes smaller than "x5", the controlling circuitry 605 is able to calculate the boundary point corresponding to the output voltage level "y1" as "x5".

Similarly, the controlling circuitry 605 determines that "x4" shall be used as a boundary point when the output voltage level is "y2". Further, the controlling circuitry 605 determines that "x3" shall be used as a boundary point when the output voltage level is "y3". Also, the controlling circuitry 605 determines that "x2" shall be used as a boundary point when the output voltage level is "y4". In addition, the controlling circuitry 605 determines that "x1" shall be used as a boundary point when the output voltage level is "y5".

As illustrated in FIG. 12, as a result of determining the output current level to serve as a boundary point for each of the output voltage levels, the controlling circuitry 605 is able to divide a plane defined by the output voltage levels and the output current levels, into "a zero current switching (ZCS) control area using the stray capacitance" and "a zero voltage switching (ZVS) control area". In this situation, the boundary points between the zero current switching control and the zero voltage switching control such as those illustrated in FIG. 12 may be calculated by the controlling circuitry 605 or may be calculated in advance so as to be acquired by the controlling circuitry 605.

For example, when starting to supply the voltage to the X-ray tube 7, the controlling circuitry 605 acquires the output voltage level and the output current level from the processing circuitry 34 and judges to which one of the control areas, namely the "ZCS control area using the stray capacitance" or the "ZVS control area", the acquired output voltage and current levels correspond. After that, on the basis of the judgment result, the controlling circuitry 605 implements one selected from between the zero current switching control and the zero voltage switching control.

Further, for example, the controlling circuitry 605 sequentially acquires output voltage levels and output current levels while X-rays are being radiated. In this situation, while the X-ray tube current modulation is being exercised, the output voltage levels and the output current levels that are sequentially acquired may not have fixed values, but may vary over the course of time, in some situations. For example, the controlling circuitry 605 acquires a fixed value "y3" as the output voltage level, and acquires, as the output current levels, values that fluctuate between a value smaller than "x3" and a value larger than "x3" depending on the X-ray tube position of the X-ray tube 7. In that situation, the controlling circuitry 605 exercises control by sequentially switching between the zero current switching control and the zero voltage switching control depending on whether the acquired output current level exceeds "x3" or not.

Further, while either the dual energy acquisition or the multi-energy acquisition is being performed with the fast kV switching scheme, the output voltage levels and the output current levels that are sequentially acquired may not have fixed values, but may vary over the course of time, in some situations. For example, the controlling circuitry 605 acquires a fixed value "x3" as the output current level, and acquires, as the output voltage levels, values that fluctuate between a value smaller than "y3" and a value larger than "y3" depending on the X-ray tube position of the X-ray tube 7. In that situation, the controlling circuitry 605 exercises control by sequentially switching between the zero current switching control and the zero voltage switching control depending on whether the acquired output voltage level exceeds "y3" or not.

In this situation, FIG. 12 illustrates only the output voltage levels and the output current levels as examples of the loads; however, possible embodiments are not limited to this example. For instance, the controlling circuitry 605 may be configured to set a threshold value for the output power level, so as to implement the zero voltage switching control when the output power exceeds the threshold value and to implement the zero current switching control when the output power does not exceed the threshold value. As another example, the controlling circuitry 605 may be configured to set a threshold value for the ON time period (duty) during the phase shift control, so as to implement the zero voltage switching control when the ON time period exceeds the threshold value and to implement the zero current switching control when the ON time period does not exceed the threshold value.

In the embodiments explained above, the constituent elements of the apparatuses and the devices are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program analyzed and executed by the CPU or may be realized as hardware using wired logic.

Further, it is possible to realize the controlling method described in any of the embodiments above by causing a computer such as a personal computer or a workstation to execute a controlling computer program (hereinafter, "controlling program") prepared in advance. The controlling program may be distributed via a network such as the Internet. Further, the controlling program may be executed as being recorded on a computer-readable recording medium such as a hard disk, flexible disk (FD), a Compact Disk Read-Only Memory (CD-ROM), a Magnetic Optical (MO) disk, a Digital Versatile Disk (DVD), or the like and being read from the recording medium by a computer.

According to at least one aspect of the embodiments described above, it is possible to reduce the switching losses in all the range from when the load is small to when the load is large.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray high voltage device comprising:
    an inverter circuit including a plurality of switching elements;
    acquiring circuitry configured to acquire information about an inverter current flowing through the inverter circuit; and
    controlling circuitry configured to determine, on a basis of the information about the inverter current, a first point in time at which the inverter current becomes substantially 0 and to exercise control by implementing zero current switching control on the switching elements at the first point in time and implementing zero voltage switching control on the switching elements at a second point in time excluding the first point in time.

2. The X-ray high voltage device according to claim 1, wherein, the controlling circuitry determines, as the first point in time, a time at which the inverter current resonating due to a stray capacitance becomes substantially 0.

3. The X-ray high voltage device according to claim 1, wherein, when exercising control so as to modulate an output current while an X-ray tube is outputting X-rays, the controlling circuitry exercises the control by implementing one selected from between the zero current switching control and the zero voltage switching control.

4. The X-ray high voltage device according to claim 2, wherein, when exercising control so as to modulate an output current while an X-ray tube is outputting X-rays, the controlling circuitry exercises the control by implementing one selected from between the zero current switching control and the zero voltage switching control.

5. The X-ray high voltage device according to claim 1, wherein, when exercising control so as to modulate output voltage while an X-ray tube is outputting X-rays, the controlling circuitry exercises the control by implementing one selected from between the zero current switching control and the zero voltage switching control.

6. The X-ray high voltage device according to claim 2, wherein, when exercising control so as to modulate output voltage while an X-ray tube is outputting X-rays, the controlling circuitry exercises the control by implementing one selected from between the zero current switching control and the zero voltage switching control.

7. An X-ray image diagnosis apparatus comprising:
    an X-ray high voltage device configured to supply high voltage;
    an X-ray tube configured to generate X-rays by using the supplied high voltage;
    an X-ray detector configured to detect X-rays radiated from the X-ray tube and to output a signal corresponding to an amount of the detected X-rays; and
    processing circuitry configured to generate a medical image on a basis of the signal, wherein
    the X-ray high voltage device includes:
        inverter circuit including a plurality of switching elements;
        acquiring circuitry configured to acquire information about an inverter current flowing through the inverter circuit; and
        controlling circuitry configured to determine, on a basis of the information about the inverter current, a first point in time at which the inverter current becomes substantially 0 and to exercise control by implementing zero current switching control on the switching elements at the first point in time and implementing zero voltage switching control on the switching elements at a second point in time excluding the first point in time.

8. An X-ray high voltage device comprising:
    an inverter circuit including a plurality of switching elements; and
    controlling circuitry configured to exercise control by implementing zero current switching control on the switching elements while an X-ray output is at a first level and implementing zero voltage switching control on the switching elements while the X-ray output is at a second level higher than the first level.

* * * * *